US008178727B2

(12) United States Patent
Shibata et al.

(10) Patent No.: US 8,178,727 B2
(45) Date of Patent: May 15, 2012

(54) BIS(ARYLMETHYLIDENE)ACETONE COMPOUND, ANTI-CANCER AGENT, CARCINOGENESIS-PREVENTIVE AGENT, INHIBITOR OF EXPRESSION OF KI-RAS, ERBB2, C-MYC AND CYCLINE D1, β-CATENIN-DEGRADING AGENT, AND P53 EXPRESSION ENHANCER

(75) Inventors: Hiroyuki Shibata, Sendai (JP);
Yoshiharu Iwabuchi, Sendai (JP);
Hisatsugu Ohori, Sendai (JP); Hiroyuki Yamakoshi, Sendai (JP); Yuichi Kakudo, Sendai (JP)

(73) Assignee: National University Corporation Tohoku University (JP)

( * ) Notice: Subject to any disclaimer, the term of this patent is extended or adjusted under 35 U.S.C. 154(b) by 390 days.

(21) Appl. No.: 11/993,840

(22) PCT Filed: Jun. 27, 2006

(86) PCT No.: PCT/JP2006/312806
§ 371 (c)(1),
(2), (4) Date: Feb. 18, 2010

(87) PCT Pub. No.: WO2007/000998
PCT Pub. Date: Jan. 4, 2007

(65) Prior Publication Data
US 2010/0152493 A1 Jun. 17, 2010

(30) Foreign Application Priority Data
Jun. 27, 2005 (JP) ................................. 2005-187394

(51) Int. Cl.
*C07C 49/217* (2006.01)
*A61K 31/12* (2006.01)
(52) U.S. Cl. ......................... 568/325; 568/327; 514/678

(58) Field of Classification Search .................. 568/325, 568/327; 514/678
See application file for complete search history.

(56) References Cited

U.S. PATENT DOCUMENTS
6,664,272 B2 * 12/2003 Snyder et al. ................. 514/327

OTHER PUBLICATIONS

Anto et al. Anticancer and antioxidant activity of synthetic chalcones and related compouds. Cancer Letters, VOl. 97, 1995, 33-37.*
Weber et al. Anti-oxidant activities of curcumin and related enones. Bioorganic & Medicinal Chemistry, vol. 13, 2005, 3811-3820.*
Adams et al. Synthesis and biological evaluation of novel curcumin analogs as anti-cancer and anti-angiogenesis agents. Bioorganic & Medicinal Chemistry, vol. 12, 2004, 3871-3883.*
Fairlamb et al. n2-dba Complexes of Pd(0): The Substituent Effect in Suzuki-Miyaura Coupling. Organic Letters, 2004, vol. 6(24), 4435-4438.*
Youssef et al. Synthesis of curcumin analogues as potential antioxidant, cancer chemopreventive agent. Archiv der Pharmazie (Weinheim, Germany), 2004, vol. 337 (1), 42-54, published online Jan. 28, 2004. HCAPLUS Accession No. 2004:116701; Document No. 141:390.*

* cited by examiner

*Primary Examiner* — Sikarl Witherspoon
(74) *Attorney, Agent, or Firm* — Hayes Soloway P.C.

(57) ABSTRACT

It has been demanded to improve the poor solubility of curcumin to develop an anti-tumor compound capable of inhibiting the growth of various cancer cells at a low concentration. Thus, disclosed is a novel synthetic compound, a bis(arylmethylidene)acetone, which has both of an excellent anti-tumor activity and a chemo-preventive activity. A bis(arylmethylidene)acetone (i.e., a derivative having a curcumin skeleton) which is an anti-tumor compound and has a chemo-preventive activity is synthesized and screened. A derivative having enhanced anti-tumor activity and chemo-preventive activity can be synthesized.

4 Claims, 15 Drawing Sheets

| Compound Name | Chemical Structure | Molecular Formula | Molecular Weight | IC50 (HCT116 μM) |
|---|---|---|---|---|
| curcumin | 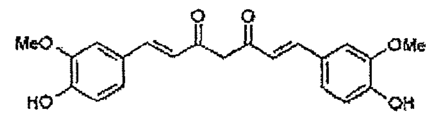 | $C_{21}H_{20}O_6$ | 368 | 6.0 |
| BDMPP (GO-035) | 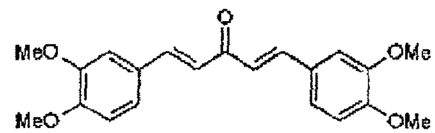 | $C_{21}H_{22}O_5$ | 354 | 1.5 |
| BTMP (GO-Y016) | 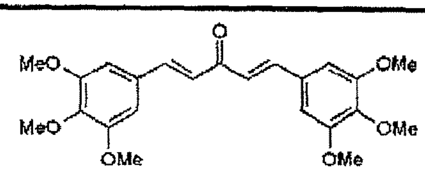 | $C_{23}H_{26}O_7$ | 414 | 0.25 |
| BBMMPP (GO-Y030) | 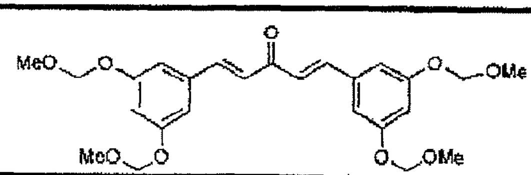 | $C_{25}H_{30}O_9$ | 474 | 0.25 |
| BDMMMPP (GO-Y031) | 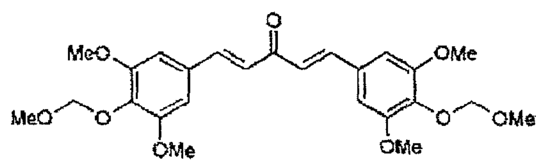 | $C_{25}H_{30}O_9$ | 474 | 0.25 |

FIG. 1

| Compound | R1 | R2 | R3 | R4 | R5 | R6 | R7 | R8 | R9 | R10 | IC$_{50}$ |
|---|---|---|---|---|---|---|---|---|---|---|---|
| GO-035 (BDMPP) | H | OCH$_3$ | OCH$_3$ | H | H | H | H | OCH$_3$ | OCH$_3$ | H | 1.5 |
| GO-949 | H | OCH$_2$O | | H | H | H | H | OCH$_2$O | | H | 25 |
| GO-Y011 | H | C$_4$H$_4$ | | H | H | H | H | C$_4$H$_4$ | | H | >100 |
| GO-Y012 | H | H | H | H | H | H | H | H | H | H | 0.75 |
| GO-Y013 | H | H | OCH$_3$ | H | H | H | H | OCH$_3$ | H | H | 9 |
| GO-Y015 | OCH$_3$ | OCH$_3$ | H | H | H | H | H | H | OCH$_3$ | OCH$_3$ | 1.3 |
| GO-Y016 (BTMP) | H | OCH$_3$ | OCH$_3$ | OCH$_3$ | H | H | OCH$_3$ | OCH$_3$ | OCH$_3$ | H | 0.25 |
| GO-Y017 | Cl | H | H | H | H | H | H | H | H | Cl | 2 |
| GO-Y018 | H | H | Br | H | H | H | H | Br | H | H | 8 |
| GO-Y019 | OCH$_3$ | H | H | H | H | H | H | H | H | OCH$_3$ | 4 |
| GO-Y020 | OCH$_3$ | OCH$_3$ | OCH$_3$ | H | H | H | H | OCH$_3$ | OCH$_3$ | OCH$_3$ | 3.5 |
| GO-Y021 | OCH$_3$ | H | OCH$_3$ | OCH$_3$ | H | H | OCH$_3$ | OCH$_3$ | H | OCH$_3$ | 2 |
| GO-Y022 | H | OCH$_3$ | OH | H | H | H | H | OH | OCH$_3$ | H | 15 |
| GO-Y023 | H | OH | OCH$_3$ | H | H | H | H | OCH$_3$ | OH | H | 0.75 |
| GO-Y026 | H | OCH$_3$ | OH | OCH$_3$ | H | H | OCH$_3$ | OH | OCH$_3$ | H | 0.8 |
| GO-Y030 BBMMPP | H | OCH$_2$OCH$_3$ | H | OCH$_2$OCH$_3$ | H | H | OCH$_2$OCH$_3$ | H | OCH$_2$OCH$_3$ | H | 0.25 |
| GO-Y031 BDMMPP | H | OCH$_3$ | OCH$_2$OCH$_3$ | OCH$_3$ | H | H | OCH$_3$ | OCH$_2$OCH$_3$ | OCH$_3$ | H | 0.25 |
| GO-Y033 | H | Br | OCH$_3$ | H | H | H | H | OCH$_3$ | Br | H | 75 |
| GO-Y035 | H | NO$_2$ | H | H | H | H | H | H | NO$_2$ | H | 3 |
| GO-Y038 | H | OH | H | OH | H | H | OH | H | OH | H | 1.5 |

FIG. 3

| Compound | R1 | R2 | R3 | R4 | R5 | R6 | R7 | R8 | R9 | R10 | IC50 |
|---|---|---|---|---|---|---|---|---|---|---|---|
| GO-Y039 | H | OCH3 | OCH2OCH2CH2OCH3 | OCH3 | H | H | OCH3 | OCH2OCH2CH2OCH3 | OCH3 | H | 0.35 |
| GO-Y040 | H | OCH2OCH3 | OCH2OCH3 | H | H | H | H | OCH2OCH3 | OCH2OCH3 | H | 0.75 |
| GO-Y044 | H | OCH3 | OCH2CH2OH | OCH3 | H | H | OCH3 | OCH2CH2OH | OCH3 | H | 0.5 |
| GO-Y046 | H | OCH3 | OCH3 | H | H | H | OCH3 | OCH3 | OCH3 | H | 0.35 |
| GO-Y047 | H | OCH3 | OCH3 | H | H | H | H | OCH3 | H | H | 4 |
| GO-Y048 | H | OCH3 | OCH2C2H | OCH3 | H | H | OCH3 | OCH2C2H | OCH3 | H | 0.25 |
| GO-Y049 | H | H | OCH3 | H | H | H | OCH3 | OCH3 | OCH3 | H | 3 |
| GO-Y050 | H | OH | OCH3 | H | H | H | H | OCH3 | OCH3 | H | 1.5 |
| GO-Y051 | H | OCH3 | OH | H | H | H | H | OCH3 | OCH3 | H | 0.7 |
| GO-Y052 | H | OCH(CH2)OCH2CH3 | OCH3 | H | H | H | H | OCH3 | OCH3 | H | 1.5 |
| GO-Y053 | H | OCH3 | OCH(CH2)OCH2CH3 | H | H | H | H | OCH3 | OCH3 | H | 0.6 |
| GO-Y055 | H | OH | OH | H | H | H | H | OCH2OCH3 | OCH3 | H | 0.8 |
| GO-Y056 | H | OH | OCH3 | H | H | H | H | OCH2OCH3 | OCH3 | H | 0.8 |
| GO-Y057 | H | OCH(CH2)OCH2CH3 | OCH3 | H | H | H | H | OCH2OCH3 | OCH3 | H | 0.7 |
| GO-Y058 | H | OCH2 | OOH(CH2)OCH2CH3 | H | H | H | H | OCH3 | OCH3 | H | 0.8 |
| GO-Y060 | H | OCH3 | OCH2C2H | OCH3 | H | H | OCH3 | H | OCH3 | H | 0.35 |
| GO-Y062 | H | OCH3 | OCH2C2H | OCH3 | H | H | OCH2OCH3 | OCH2OCH3 | OCH3 | H | 0.35 |
| GO-Y063 | H | OCH3 | OCH2C2H | H | H | H | OCH3 | OCH3 | OCH2OCH3 | H | 0.4 |
| GO-Y085 | H | OCH3 | OCH2CH2N3 | OCH3 | H | H | OCH3 | OCH2CH2N3 | OCH3 | H | 0.4 |
| GO-Y087 | H | OCH3 | H | OCH3 | H | H | OCH3 | H | OCH3 | H | 0.35 |

FIG. 4

FACScan
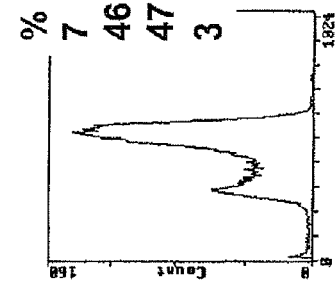
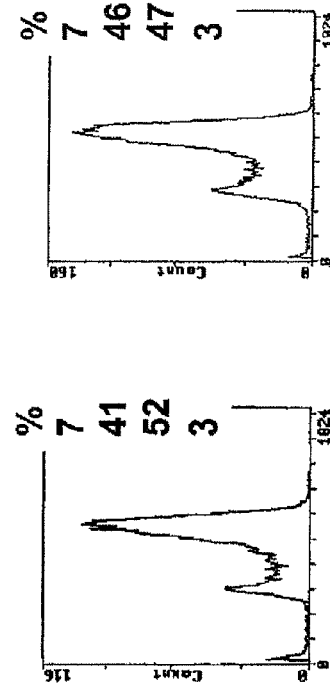
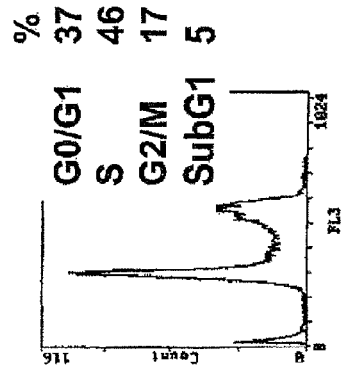
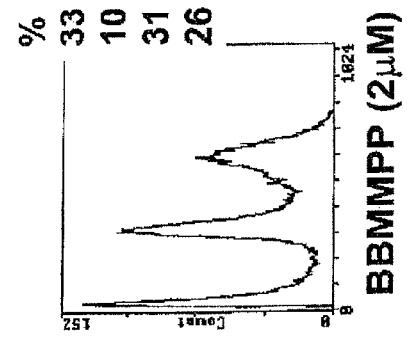
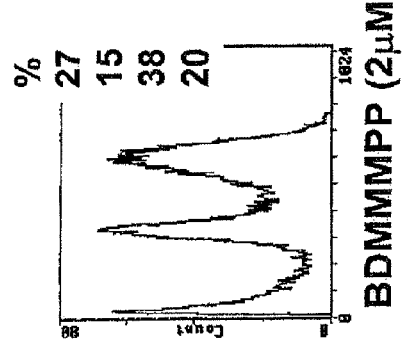
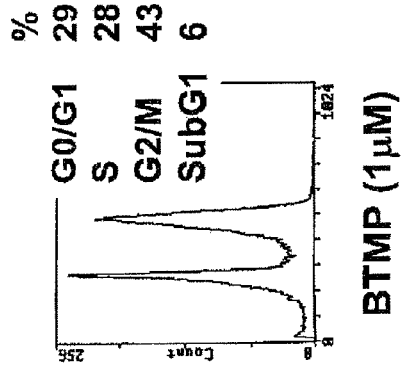
FIG. 7A Control (DMSO 1%)
FIG. 7B Curcumin (20μM)
FIG. 7C BDMPP (5μM)
FIG. 7D BTMP (1μM)
FIG. 7E BDMMPP (2μM)
FIG. 7F BBMMPP (2μM)

BIS(ARYLMETHYLIDENE)ACETONE COMPOUND, ANTI-CANCER AGENT, CARCINOGENESIS-PREVENTIVE AGENT, INHIBITOR OF EXPRESSION OF KI-RAS, ERBB2, C-MYC AND CYCLINE D1, β-CATENIN-DEGRADING AGENT, AND P53 EXPRESSION ENHANCER

TECHNICAL FIELD

The present invention relates to a novel pharmacological agent that is used for inhibiting the growth of various cancer cells and for preventing carcinogenesis. The present invention also relates to novel bis(arylmethylidene)-acetones and salts thereof.

BACKGROUND ART

Curcumin (diferuloylmethane or (1E,6E)-1,7-bis(4-hydroxy-3-methoxyphenyl)-1,6-heptadiene-3,5-dione) is contained in turmeric (Curcuma longa L.), which is a yellow pigment used as a spice. Curcumin exerts inhibitory activity in the growth of various cancer cells, including, e.g., colon cancer, breast cancer, and prostate cancer. Curcumin is well-known from investigations in mouse models to be active in preventing carcinogenesis and inhibiting the occurrence of adenomas, which are precancerous lesions of colon cancer.

The activity in inhibiting the growth of cancer cells, the anti-carcinogenic activity, and other pharmacological activities of curcumin are described in, e.g., Non-Patent Documents 1, 2, 3. Non-Patent Document 1 describes the effect of curcumin in inhibiting the growth of colon cancer cells at a concentration of 20 μM and in degrading β-catenin at a concentration of 15 μM. However, the water-solubility of curcumin is poor, and improving the activity of inhibiting cell growth is difficult.

Curcumin-like compounds such as 1,5-bis(3,4-dimethoxyphenyl)-1,4-pentadien-3-one (BDMPP) that have improved water-solubility and enhanced activity are described in Non-Patent Document 2, but the compounds BDMMMPP and BBMMPP synthesized in the present invention are not described therein, and BTMP is also not described. A description of the anti-carcinogenic activity of BDMPP is also not present.

Non-Patent Document 3 describes a decrease of approximately 40% in the occurrence of adenomas, which are pre-cancerous lesions, after oral administration of curcumin having β-catenin-degrading activity in a mouse strain having a high incidence of colon cancer, but there is no description of the synthesis of the compound having strong β-catenin-degrading activity. A method for synthesizing BTMP is described in Non-Patent Document 4, but this document does not contain a description of the anti-cancer effect thereof.

Non-Patent Document 1: Jaiswal A. S. et al., Oncogene, 21, pp. 8414-8427 "β-Catenin-mediated transactivation and cell-cell adhesion pathways are important in curcumin (diferuylmethane)-induced growth arrest and apoptosis in colon cancer cells," 2002.

Non-Patent Document 2: Adams B. K. et al., Bioorganic & Medicinal Chemistry, 12, pp. 3871-3883 "Synthesis and biological evaluation of novel curcumin analogs as anti-cancer and anti-angiogenesis agents," 2004.

Non-Patent Document 3: Perkins S. et al., Cancer Epidemiology, Biomarkers & Prevention, 11, pp. 535-540 "Chemopreventive efficacy and pharmacokinetics of curcumin in the Min/+mouse, a model of familial adenomatous polyposis," 2002.

Non-Patent Document 4: Esther Caballero et al., Tetrahedron, 54, pp. 6111-6122 "Synthesis of (±)-7-(3,4,5-trimethoxyphenyl)-7-deoxyidarubicinone. A new family of anthracycline analogues," 1998.

DISCLOSURE OF THE INVENTION

Problems to be Solved by the Invention

Curcumin and known analogues as described above have relatively weak activity in limiting cancer-cell proliferation and preventing carcinogenesis. These compounds have low bioavailability, such as the activity in limiting cancer-cell proliferation and preventing carcinogenesis in living organisms.

It is an object of the present invention to provide a drug that has significantly increased activity in inhibiting cancer-cell growth and preventing carcinogenesis, especially has extremely strong activity in inhibiting tumor growth and preventing the carcinogenesis of colon cancer and various other cancers.

Means for Solving the Aforementioned Problems

The present invention provides orally administrable compounds having potent inhibitory activity in the growth of colon cancer cells and various other cancer cells; and having growth inhibitory activity against cancer cells, at least equal to or greater than curcumin. The present invention also provides pharmaceutical compositions, pharmaceutical drugs or agents and other active drug preparations that have significantly increased inhibitory activity in cancer-cell growth and carcinogenesis; and have extremely strong activity in inhibiting the development and growth and/or preventing the genesis of colon cancer and various other cancers.

In one aspect, the present invention provides the following:

[1] An inhibitor of Ki-Ras, ErbB2, c-Myc, or Cyclin D1 expression; a β-catenin-degrading agent; a p53 expression enhancer; an anti-cancer agent; or an anti-carcinogenic agent, which comprises an effective amount of a compound, or a salt thereof, of Formula (1):

[Chemical Structure 1]

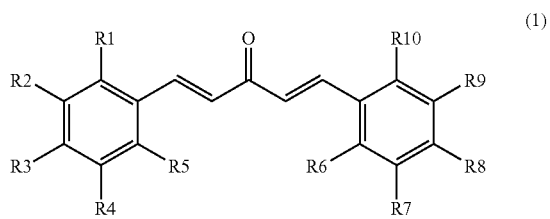

(1)

(wherein R1 to R10 may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or two substituents when present on adjacent carbon atoms on the phenyl ring can be taken together to form an alkylene-dioxy bridge or an alkylene bridge).

[2] The agent according to [1], wherein the bis(arylmethylidene)-acetone compound or a salt thereof is selected from the group consisting of (1E,4E)-(1,5-diphenyl)penta-1,4-dien-3-one (GO-Y012), (1E,4E)-1,5-bis-(3,4,5-trimethoxyphenyl)penta-1,4-dien-3-one (GO-Y016. BTMP), (1E,4E)-

1,5-bis-(3-hydroxy-4-methoxyphenyl)penta-1,4-dien-3-one (GO-Y023), (1E,4E)-1,5-bis-(4-hydroxy-3,5-dimethoxyphenyl)penta-1,4-dien-3-one (GO-Y026), (1E,4E)-1,5-bis-(3,5-bismethoxymethoxyphenyl)penta-1,4-dien-3-one (GO-Y030 BBMMPP), (1E,4E)-1,5-bis-(3,5-dimethoxy-4-methoxymethoxyphenyl)penta-1,4-dien-3-one (GO-Y031, BDMMMPP), (1E,4E)-1,5-bis-(3,5-dimethoxy-4-methoxyethoxyphenyl)penta-1,4-dien-3-one (GO-Y039), (1E,4E)-1,5-bis-(3,4-bismethoxymethoxyphenyl)penta-1,4-dien-3-one (GO-Y040), (1E,4E)-1,5-bis-[4-(2-hydroxyethoxy)-3,5-dimethoxyphenyl]penta-1,4-dien-3-one (GO-Y044), (1E,4E)-1-(3,4-dimethoxyphenyl)-5-(3,4,5-trimethoxyphenyepenta-1,4-dien-3-one (GO-Y046), (1E,4E)-1,5-bis-(3,5-dimethoxy-4-prop-2-ynyloxyphenyl)penta-1,4-dien-3-one (GO-Y048), (1E,4E)-5-(3,4-dimethoxyphenyl)-1-(4-hydroxy-3-methoxyphenyepenta-1,4-dien-3-one (GO-Y051), (1E,4E)-5-(3,4-dimethoxyphenyl)-1-[4-(1-ethoxyethoxy)-3-methoxyphenyl]penta-1,4-dien-3-one (GO-Y053), (1E,4E)-1-(4-hydroxy-3-methoxyphenyl)-5-(3-methoxy-4-methoxymethoxy-phenyl)penta-1,4-dien-3-one (GO-Y055), (1E,4E)-1-(3-hydroxy-4-methoxyphenyl)-5-(3-methoxy-4-methoxymethoxy-phenyl)penta-1,4-dien-3-one (GO-Y056), (1E,4E)-1-[3-(1-ethoxyethoxy)-4-methoxyphenyl]-5-(3-methoxy-4-methoxy-methoxyphenyl)penta-1,4-dien-3-one (GO-Y057), (1E,4E)-1-[4-(1-ethoxyethoxy)-3-methoxyphenyl]-5-(3-methoxy-4-methoxymethoxyphenyl)penta-1,4-dien-3-one (GO-Y058), (1E,4E)-1-(3,5-dimethoxy-4-prop-2-ynyloxyphenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxyphenyl)penta-1,4-dien-3-one (GO-Y062), (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063), (1E,4E)-1,5-bis-[4-(2-azidoethoxy)-3,5-dimethoxyphenyl]-penta-1,4-dien-3-one (GO-Y065), (1E,4E)-1,5-bis-(3,5-dimethoxymethoxyphenyl)penta-1,4-dien-3-one (GO-Y067), and salts thereof.

[3] A bis(arylmethylidene)-acetone compound, or a salt thereof, having the Formula (2):

[Chemical Structure 2]

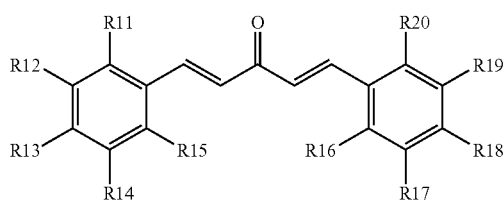

(2)

(wherein R11 through R20 may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or two substituents when present on adjacent carbon atoms on the phenyl ring can be taken together to form an alkylene-dioxy bridge or an alkylene bridge; provided that (1) compounds in which R12, R13, R18, and R19 are all methoxy groups and in which R11, R14, R15, R16, R17, and R20 are all hydrogen atoms are excluded, and
(2) compounds in which R12, R13, R14, R17, R18, and R19 are all methoxy groups and in which R11, R15, R16, and R20 are all hydrogen atoms are excluded).

[4] The bis(arylmethylidene)-acetone compound according to [3] or a salt thereof, which is selected from the group consisting of (1E,4E)-(1,5-diphenyl)penta-1,4-dien-3-one (GO-Y012), (1E,4E)-1,5-bis-(4-methoxyphenyl)penta-1,4-dien-3-one (GO-Y013), (1E,4E)-1,5-bis-(2,3-dimethoxyphenyl)penta-1,4-dien-3-one (GO-Y015). (1E,4E)-1,5-bis-(2-chlorophenyl)penta-1,4-dien-3-one (GO-Y017), (1E,4E)-1,5-bis-(4-bromophenyl)penta-1,4-dien-3-one (GO-Y018), (1E,4E)-1,5-bis-(2-methoxyphenyl)penta-1,4-dien-3-one (GO-Y019), (1E,4E)-1,5-bis-(2,3,4-trimethoxyphenyl)penta-1,4-dien-3-one (GO-Y020), (1E,4E)-1,5,-bis-(2,4,5-trimethoxyphenyl)penta-1,4-dien-3-one (GO-Y021), (1E,4E)-1,5-bis-(3-hydroxy-4-methoxyphenyl)penta-1,4-dien-3-one (GO-Y023), (1E,4E)-1,5-bis-(4-hydroxy-3,5-dimethoxyphenyl)penta-1,4-dien-3-one (GO-Y026), (1E,4E)-1,5-bis-(3,5-bismethoxymethoxyphenyl)penta-1,4-dien-3-one (GO-Y030, BBMMPP), (1E,4E)-1,5-bis-(3,5-dimethoxy-4-methoxymethoxy-phenyl)penta-1,4-dien-3-one (GO-Y031, BDMMMPP), (1E,4E)-1,5-bis-(3-nitrophenyl)-penta-1,4-dien-3-one (GO-Y035), (1E,4E)-1,5-bis-(3,5-dihydroxyphenyl)penta-1,4-dien-3-one (GO-Y038), (1E,4E)-1,5-bis-(3,5-dimethoxy-4-methoxyethoxymethoxy-phenyl)penta-1,4-dien-3-one (GO-Y039), (1E,4E)-1,5-bis-(3,4-bismethoxymethoxyphenyl)penta-1,4-dien-3-one (GO-Y040), (1E,4E)-1,5-bis-[4-(2-hydroxyethoxy)-3,5-dimethoxyphenyl]penta-1,4-dien-3-one (GO-Y044), (1E,4E)-1-(3,4-dimethoxyphenyl)-5-(3,4,5-trimethoxyphenyl)penta-1,4-dien-3-one (GO-Y046), (1E,4E)-1-(3,4-dimethoxyphenyl)-5-(4-methoxyphenyl)penta-1,4-dien-3-one (GO-Y047), (1E,4E)-1,5-bis-(3,5-dimethoxy-4-prop-2-ynyloxyphenyl)penta-1,4-dien-3-one (GO-Y048), (1E,4E)-1-(4-methoxyphenyl)-5-(3,4,5-trimethoxyphenyl)penta-1,4-dien-3-one (GO-Y049), (1E,4E)-5-(3,4-dimethoxyphenyl)-1-(3-hydroxy-4-methoxyphenyl)penta-1,4-dien-3-one (GO-Y050), (1E,4E)-5-(3,4-dimethoxyphenyl)-1-(4-hydroxy-3-methoxyphenyl)penta-1,4-dien-3-one (GO-Y051), (1E,4E)-5-(3,4-dimethoxyphenyl)-1-[3-(1-ethoxyethoxy)-4-methoxyphenyl]penta-1,4-dien-3-one (GO-Y052), (1E,4E)-5-(3,4-dimethoxyphenyl)-1-[4-(1-ethoxyethoxy)-3-methoxyphenyl]penta-1,4-dien-3-one (GO-Y053), (1E,4E)-1-(4-hydroxy-3-methoxyphenyl)-5-(3-methoxy-4-methoxymethoxy-phenyl)penta-1,4-dien-3-one (GO-Y055), (1E,4E)-1-(3-hydroxy-4-methoxyphenyl)-5-(3-methoxy-4-methoxymethoxy-phenyl)penta-1,4-dien-3-one (GO-Y056), (1E,4E)-1-[3-(1-ethoxyethoxy)-4-methoxyphenyl]-5-(3-methoxy-4-methoxy-methoxyphenyl)penta-1,4-dien-3-one (GO-Y057), (1E,4E)-1-[4-(1-ethoxyethoxy)-3-methoxyphenyl]-5-(3-methoxy-4-methoxy-methoxyphenyl)penta-1,4-dien-3-one (GO-Y058), (1E,4E)-1-(3,5-dimethoxy-4-prop-2-ynyloxyphenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxy-phenyl)penta-1,4-dien-3-one (GO-Y062), (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063), (1E,4E)-1,5-bis-[4-2-(azidoethoxy)-3,5-dimethoxyphenyl]penta-1,4-dien-3-one (GO-Y065), (1E,4E)-1,5-bis-(3,5-dimethoxy-methoxyphenyl)penta-1,4-dien-3-one (GO-Y067), 1,5-bis(3,4,5-trimethoxyphenyl)penta-1,4-dien-3-one, and salts thereof.

In another aspect, the present invention provides the following:

[5] An anti-cancer agent, which comprises an effective amount of a bis(arylmethylidene)-acetone compound, or a salt thereof, having the Formula (4):

[Chemical Structure 3]

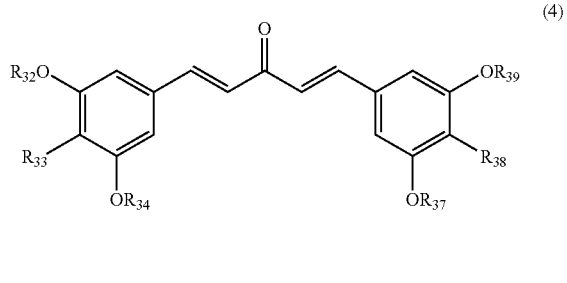

(4)

[Chemical Structure 4]

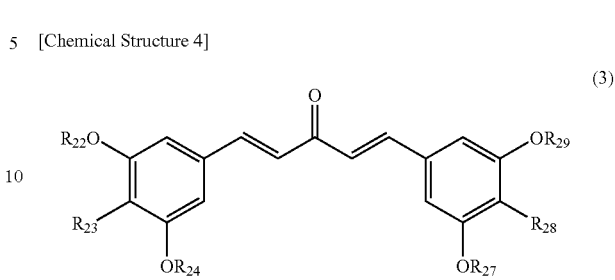

(3)

(wherein $R_{33}$ and $R_{38}$ may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or $R_{33}$ may be taken together with the adjacent substituent $OR_{32}$ or $OR_{34}$ to form an alkylene-dioxy bridge, and/or, $R_{38}$ may be taken together with the adjacent substituent $OR_{37}$ or $OR_{39}$ to form an alkylene-dioxy bridge; and $R_{32}$, $R_{34}$, $R_{37}$, and $R_{39}$ may be the same or different and are each independently a member selected from the group consisting of a hydrogen atom, an alkyl group, an alkoxyalkyl group, an alkoxyalkoxyalkyl group, and an azido-alkyl group, or may be taken together with the adjacent substituent $R_{33}$ or $R_{38}$ to form the aforementioned bridge).

[6] The anti-tumor agent according to [5], wherein the bis(arylmethylidene)-acetone compound or a salt thereof is selected from the group consisting of (1E,4E)-1,5-bis-(3,4,5-trimethoxyphenyl)penta-1,4-dien-3-one (GO-Y016, BTMP), (1E,4E)-1,5-bis-(4-hydroxy-3,5-dimethoxyphenyl)penta-1,4-dien-3-one (GO-Y026), (1E,4E)-1,5-bis-(3,5-bis-methoxymethoxyphenyl)penta-1,4-dien-3-one (GO-Y030, BBMMPP), (1E,4E)-1,5-bis-(3,5-dimethoxy-4-methoxymethoxyphenyl)penta-1,4-dien-3-one (GO-Y031, BDMMPP), (1E,4E)-1,5-bis-(3,5-dimethoxy-4-methoxyethoxymethoxyphenyl)penta-1,4-dien-3-one (GO-Y039), (1E,4E)-1,5-bis-[4-(2-hydroxyethoxy)-3,5-dimethoxyphenyl]penta-1,4-dien-3-one (GO-Y044), (1E,4E)-1,5-bis-(3,5-dimethoxy-4-prop-2-ynyloxyphenyl)penta-1,4-dien-3-one (GO-Y048), (1E,4E)-1-(3,5-dimethoxy-4-prop-2-ynyloxyphenyl)-5-(3,4,5-trimethoxy-phenyl)penta-1,4-dien-3-one (GO-Y060), (1E,4E)-1-(3,5-bis-methoxymethoxyphenyl)-5-(3,5-dimethoxy-4-prop-2-ynyloxy-phenyl)penta-1,4-dien-3-one (GO-Y062), (1E,4E)-1,5-bis-[4-(2-azidoethoxy)-3,5-dimethoxyphenyl]penta-1,4-dien-3-one (GO-Y065), and (1E,4E)-1,5-bis-(3,5-dimethoxymethoxy-phenyl)penta-1,4-dien-3-one (GO-Y067).

[7] An anti-carcinogenic agent, which comprises an effective amount of a bis(arylmethylidene)-acetone compound, or a salt thereof, having the Formula (4) (wherein $R_{32}$, $R_{33}$, $R_{34}$, $R_{37}$, $R_{38}$, and $R_{39}$ have the same meanings as defined in [5] above).

[8] An inhibitor of Ki-Ras, ErbB2, c-Myc, or Cyclin D1 expression; a β-catenin-degrading agent; or a p53 expression enhancer, which comprises an effective amount of a bis(arylmethylidene)-acetone compound, or a salt thereof, having the Formula (4) (wherein $R_{32}$, $R_{33}$, $R_{34}$, $R_{37}$, $R_{38}$, and $R_{39}$ have the same meanings as defined in [5] above).

[9] A bis(arylmethylidene)-acetone compound, or a salt thereof, having the Formula (3):

(wherein $R_{23}$ and $R_{28}$ may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or $R_{23}$ may be taken together with the adjacent substituent $OR_{22}$ or $OR_{24}$ to form an alkylene-dioxy bridge, and/or $R_{28}$ may be taken together with the adjacent substituent $OR_{27}$ or $OR_{29}$ to form an alkylene-dioxy bridge; and $R_{22}$, $R_{24}$, $R_{27}$, and $R_{29}$ may be the same or different and are each independently a member selected from the group consisting of a hydrogen atom, an alkyl group, an alkoxyalkyl group, an alkoxyalkoxyalkyl group, and an azido-alkyl group, or may be taken together with the adjacent substituent $R_{23}$ or $R_{28}$ to form the aforementioned bridge; provided that compounds in which $R_{23}$ and $R_{28}$ are both methoxy groups are excluded)

[10] The bis(arylmethylidene)-acetone compound according to [9] or a salt thereof, selected from the group consisting of (1 E,4E)-1,5-bis-(4-hydroxy-3,5-dimethoxy-phenyl) penta-1,4-dien-3-one (GO-Y026), (1E,4E)-1,5-bis-(3,5-bis-methoxymethoxyphenyl)penta-1,4-dien-3-one (GO-Y030, BBMMPP), (1E,4E)-1,5-bis-(3,5-dimethoxy-4-methoxymethoxyphenyl)penta-1,4-dien-3-one (GO-Y031, BDMMMPP), (1E,4E)-1,5-bis-(3,5-dimethoxy-4-methoxyethoxymethoxyphenyl)penta-1,4-dien-3-one (GO-Y039), (1E,4E)-1,5-bis-[4-(2-hydroxyethoxy)-3,5-dimethoxy-phenyl]penta-1,4-dien-3-one (GO-Y044), (1E,4E)-1,5-bis-(3,5-dimethoxy-4-prop-2-ynyloxyphenyl)penta-1,4-dien-3-one (GO-Y048), (1E,4E)-1-(3,5-dimethoxy-4-prop-2-ynyloxyphenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxyphenyl)penta-1,4-dien-3-one (GO-Y062), (1E,4E)-1,5-bis-[4-(2-azidoethoxy)-3,5-dimethoxyphenyl)-penta-1,4-dien-3-one (GO-Y065), (1E, 4E)-1,5-bis-(3,5-dimethoxymethoxy-phenyl)penta-1,4-dien-3-one (GO-Y067), 1,5-bis(3,4,5-trimethoxyphenyl)penta-1,4-dien-3-one, and salts thereof.

ADVANTAGEOUS EFFECTS OF THE INVENTION

According to the present invention, pharmaceutical compositions, pharmaceutical drugs or other biologically active agents are provided having strong activity in inhibiting the growth of cancer cells and/or preventing carcinogenesis and comprising an effective amount of at least one member selected from bis(arylmethylidene)acetone compounds or salts thereof, resulting from chemically structural modifications based on the basic chemical skeleton of curcumin. The growth of cancer cells and/or carcinogenesis can be inhibited using the inventive compound, and further research in these areas will be achievable. In the present invention, curcumin is used as a basic skeleton, modifications are made to the chemical structure, and derivative compounds that have high activity in inhibiting cancer-cell growth and/or preventing carcinogenesis and that also have excellent water-solubility can be synthesized and put to use. Effects of inhibiting growth and preventing carcinogenesis of various types of cancer can thereby be obtained.

The above objects and other objects, features, advantages, and aspects of the present invention are readily apparent to those skilled in the art from the following disclosures. It should be understood, however, that the description of the specification including the following best modes of carrying out the invention, specific examples, etc. is illustrating preferred embodiments of the present invention and given only for illustrative purposes. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the documents cited herein for illustrative purposes are hereby incorporated by reference into the present disclosure.

BRIEF DESCRIPTION OF THE DRAWINGS

FIG. 1 shows the chemical structures, molecular weights, and effects of inhibiting growth (IC50) of HCT116 colon cancer cells for BBMMPP (GO-Y030) and BDMMMPP (GO-Y031), which were synthesized in present invention, and for curcumin, BDMPP (GO-035), and BTMP (GO-Y016);

FIG. 3 shows the substituent groups and the activity (IC50) in inhibiting growth of HCT116 colon cancer cells for the bis(arylmethylidene)-acetone compounds of General Formula (1) (continued in FIG. 4);

FIG. 4 shows the substituent groups and the activity (IC50) in inhibiting growth of HCT116 colon cancer cells for the bis(arylmethylidene)-acetone compounds of General Formula (1) (continued from FIG. 3);

FIGS. 7A-7F show the effects of curcumin, BDMPP (GO-035), BTMP (GO-Y016), BDMMMPP (GO-Y031), and BBMMPP (GO-Y030) on the cell cycle, demonstrating that colon cancer cells are arrested in the G2/M phase at lower concentrations of BDMPP (GO-035), BTMP (GO-Y016), BDMMMPP (GO-Y031), and BBMMPP (GO-Y030) according to cell-cycle analysis using a flow cytometer, and that cell death due to induction of apoptosis (shown by the "sub-G1" fraction) is instigated by lower concentrations of BDMMMPP (GO-Y031) and BBMMPP (GO-Y030);

BEST MODE FOR CARRYING OUT THE INVENTION

The compounds of the present invention and the effects exerted by those compounds will be described below with reference to the drawings. Curcumin (FIG. 1) is a naturally-derived organic compound contained in turmeric and is well-known for inhibiting the growth of various types of cancer cells. Many of the details of the mechanism of this effect remain unclear, but curcumin limits the transcription-activating capability of the transcription factors NF-κB and AP-1, which are active in many cancer cells, whereby a group of genes that are involved in cell growth and that are controlled by these transcription factors are controlled and inhibited. Curcumin is also known to be active in degrading the transcription factor $\beta$-catenin, which is involved in the initiation of carcinogenesis in the colon. Curcumin is known to be active in preventing carcinogenesis in the colon from analyses using mouse models which actually undergo colon carcinogenesis. It is thought that the creation of derivatives in which these activities of curcumin have been enhanced would result in the development of even more effective cancer-treatment drugs and anti-carcinogenic drugs.

Figure 2:
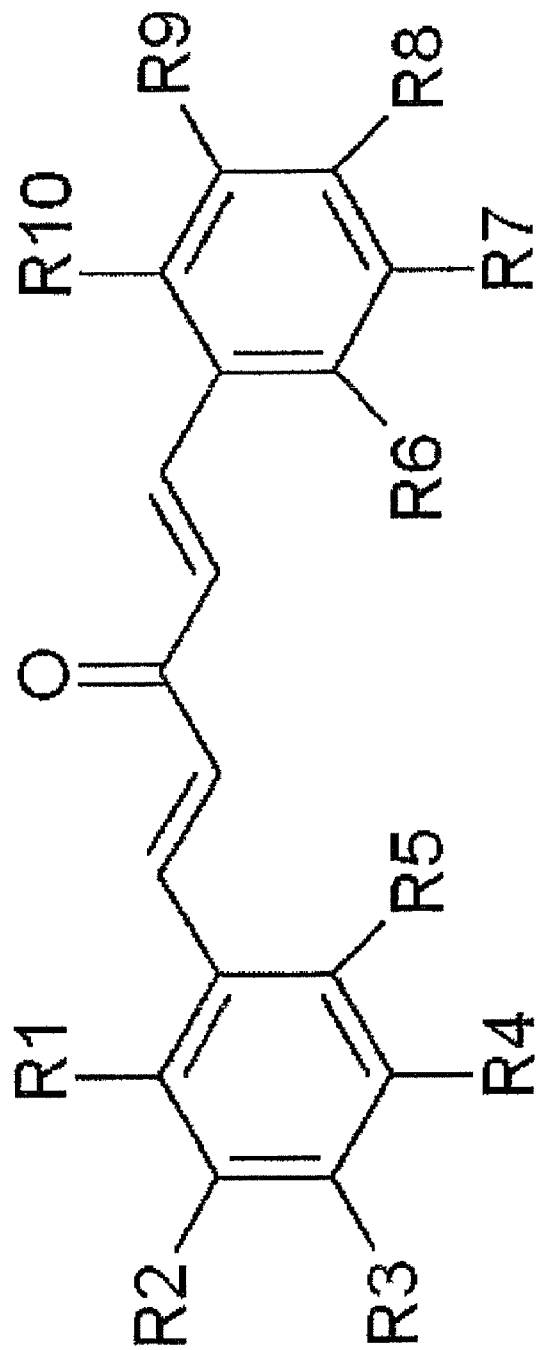
FIG. 2 shows the basic skeleton for a bis(arylmethylidene)-acetone compound according to the present invention, wherein R1 through R10 are substituent groups on the two benzene rings of various derivatives.

1,5-Bis(3,4-dimethoxyphenyl)-penta-1,4-dien-3-one (BDMPP (GO-035)) (FIG. 1) is a remodeled derivative based on the basic β-diketone skeleton of curcumin, wherein a mono-ketone structure is substituted for the basic skeleton. This compound has been recognized as having an enhanced activity of inhibiting the growth of melanoma and breast cancer cells. The efficacy is approximately 1.3 to 2.1 times that of curcumin (see the aforementioned Non-Patent Document 2). BDMPP has been improved upon in the present invention. Compounds have been synthesized with a variety of substituents being added to or introduced into the benzene rings in the first and fifth positions on both ends for BDMPP. This group of compounds are denoted by the name "bis(arylmethylidene) acetones" (FIG. 2). Representatives of the bis(arylmethylidene)-acetone compounds according to the present invention are those compounds having the Formula (1):

[Chemical Structure 5]

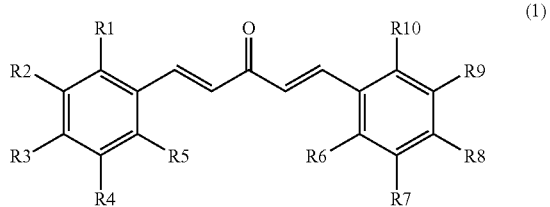

(1)

(wherein R1 through R10 may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or two substituents when present on adjacent carbon atoms on the phenyl ring can be taken together to form an alkylene-dioxy bridge or an alkylene bridge), or salts thereof.

As used herein, the "alkyl", "alkenyl", or "alkynyl" moiety in the "alkoxy group", "alkoxyalkoxy group", "alkoxyalkoxyalkoxy group", and "azido-alkoxy group" may be straight chains or branched chains, and may be saturated or unsaturated. The alkyl, alkenyl, or alkynyl moieties are preferably alkyl groups, alkenyl groups, alkynyl groups, or alkylene chains, alkenylene chains, or alkynylene chains derived from these groups. Examples of the alkyl groups include lower alkyl groups having 1 to 4 carbons and alkyl groups having 4 or more carbons. Examples of the alkenyl groups and alkynyl groups include lower alkenyl or alkynyl groups having 2 to 4 carbons and alkenyl or alkynyl groups having 4 or more carbons. Carbon chains of these compounds may include unsaturated bonds, e.g., mixtures of double and triple bonds. Examples of groups that may be used include methyl, ethyl, propyl, isopropyl, butyl, isobutyl, sec-butyl, tert-butyl, pentyl, isopentyl, tert-pentyl, hexyl, heptyl, octyl, nonyl, decanyl, hexadecanyl, and eicosanyl. Additional examples include $C_{2-24}$ alkenyl groups (e.g., vinyl, allyl, isopropenyl, 1-butenyl, 2-butenyl, 3-butenyl, 2-methyl-2-propenyl, 1-methyl-2-propenyl, and 2-methyl-1-propenyl groups), $C_{2-6}$ alkynyl groups (e.g., ethynyl, propargyl, 1-butynyl, 2-butynyl, 3-butynyl, and 1-hexynyl groups), and $C_{3-8}$ cycloalkyl groups (e.g., cyclopropyl, cyclobutyl, cyclopentyl, 2-cyclopenten-1-yl, cyclohexyl, 1,3-cyclohexadienyl, cycloheptyl, and spiro[4.5]decanyl groups). The alkyl groups are preferably $C_{1-4}$ lower alkyl groups, e.g., methyl, ethyl, propyl, isopropyl, butyl, or tert-butyl groups. The alkynyl groups are preferably $C_{2-4}$ lower alkynyl groups, e.g., ethynyl, propargyl, or 1-butynyl groups.

Representatives of the "alkoxy group" include methoxy, ethoxy, and prop-2-ynyloxy. A preferable alkoxy group is methoxy and the like. Representatives of the "alkoxyalkoxy group" include methoxymethoxy, methoxyethoxy, 1,2-bismethoxyethoxy, and prop-2-ynyloxymethoxy. A preferable alkoxyalkoxy group is methoxymethoxy and the like. Representatives of the "alkoxyalkoxyalkoxy group" include methoxymethoxymethoxy, methoxymethoxyethoxy, methoxyethoxymethoxy, ethoxymethoxymethoxy, and 1,2-bismethoxyethoxymethoxy. A preferable alkoxyalkoxyalkoxy group is methoxymethoxymethoxy and the like. The "alkylenedioxy bridge" may be alkylene chains substituted with one or more alkyl and/or alkoxy groups, wherein the alkyl and alkoxy groups are selected from those described above. Representatives of the "alkylenedioxy bridge" include methylenedioxy, ethylenedioxy, and trimethylenedioxy. A preferable alkylenedioxy bridge is methylenedioxy and the like. Representatives of the "alkylene bridge" include methylene, ethylene, trimethylene, and tetramethylene. A preferable alkylene bridge is tetramethylene and the like. Examples of the "halogen atom" include fluorine, chlorine, bromine, and iodine.

Representatives of the novel bis(arylmethylidene)-acetone compound according to the present invention are a bis(arylmethylidene)-acetone compound, or a salt thereof, having the Formula (2):

[Chemical Structure 6]

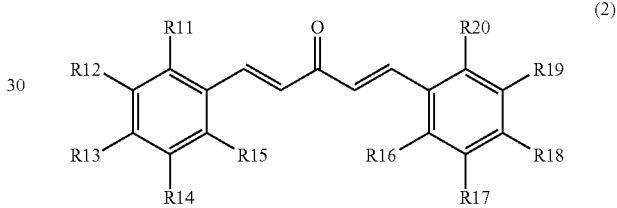

(2)

(wherein R11 to R20 may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or two substituents when present on adjacent carbon atoms on the phenyl ring can be taken together to form an alkylenedioxy bridge or an alkylene bridge; provided that (1) compounds in which R12, R13, R18, and R19 are all methoxy groups and in which R11, R14, R15, R16, R17, and R20 are all hydrogen atoms are excluded, and
(2) compounds in which R12, R13, R14, R17, R18, and R19 are all methoxy groups and in which R11, R15, R16, and R20 are all hydrogen atoms are excluded).

Further examples of the novel compound according to the present invention are bis(arylmethylidene)-acetone compounds or their salts, having the Formula (3):

[Chemical Structure 7]

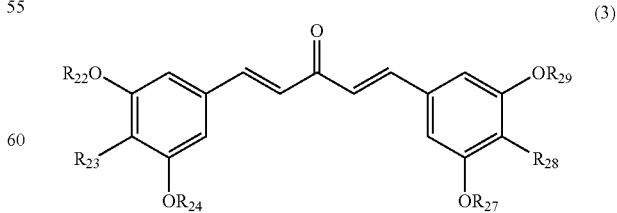

(3)

(wherein $R_{23}$ and $R_{28}$ may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or $R_{23}$ may be taken together with the adjacent substituent $OR_{22}$ or $OR_{24}$ to form an alkylene-dioxy bridge, and/or $R_{28}$ may be taken together with the adjacent substituent $OR_{27}$ or $OR_{29}$ to form an alkylene-dioxy bridge; and $R_{22}$, $R_{24}$, $R_{27}$, and $R_{29}$ may be the same or different and are each independently a member selected from the group consisting of a hydrogen atom, an alkyl group, an alkoxyalkyl group, an alkoxyalkoxyalkyl group, and an azido-alkyl group, or may be taken together with the adjacent substituent $R_{23}$ or $R_{28}$ to form the aforementioned bridge; provided that compounds in which $R_{23}$ and $R_{28}$ are both methoxy groups are excluded).

Examples of the aforementioned "alkyl group," "alkoxyalkyl group," "alkoxyalkoxyalkyl group," and "azido-alkyl group" include those groups corresponding to the groups described for the "alkoxy group", "alkoxyalkoxy group", "alkoxyalkoxyalkoxy groups", and "azido-alkoxy group" in relation to the aforementioned Formula (1).

The bis(arylmethylidene)-acetones as disclosed herein can be obtained by condensing a corresponding aryl aldehydes with acetone; e.g., an aryl aldehyde of Formula (5) may be condensed with acetone (6) at one aryl aldehyde molecule: one acetone molecule ratio to afford a compound of Formula (7). The resulting compound of Formula (7) is then condensed with an aryl aldehyde of General Formula (8) at a molecule ratio of 1:1, allowing the production of bis(arylmethylidene)-acetone. Alternatively, symmetrical bis(arylmethylidene)-acetones can be obtained when two molecules of the aryl aldehyde of General Formula (5) are condensed with one molecule of acetone (6).

and the aryl aldehyde compound (5) in an aqueous solution under basic conditions using, e.g., a 1:2 ratio of acetone/aryl aldehyde compound (5) or a larger amount of the aryl aldehyde compound (5).

The non-symmetrical bis(arylmethylidene)-acetone compound of General Formula (1) can be obtained by, e.g., causing a reaction using a 4:1 ratio of acetone/aryl aldehyde compound (5) or a smaller amount of the aryl aldehyde compound (5), synthesizing the compound of General Formula (7), performing isolation and purification as necessary, and then reacting the compound of General Formula (7) with the aryl aldehyde of General Formula (8). The reactions are preferably performed in aqueous solution under basic conditions.

The reactions of the present invention can be performed in the absence of a solvent (including cases in which a reactant serves as the solvent) or advantageously in the presence of a solvent that is inert in the reaction. The solvent is not particularly limited as long as the reaction proceeds, but aqueous solvents are preferably employed; e.g., water, methanol, ethanol, n-propanol, isopropanol, cyclohexanol, furfuryl alcohol, ethylene glycol, benzyl alcohol, and other alcohols; benzene, toluene, xylene, ethylbenzene, cumene, and other aromatic hydrocarbons; solvent naphtha, petroleum ether, and ligroin; dichloromethane, dichloroethane, chloroform, dichlorohexane, and other halogenated hydrocarbons; 2-methylbutane, n-hexane, isohexane, n-heptane, octane, nonane, decane, 2-methylpentane, 2,2-dimethylbutane, 2,3-dimethylbutane, 2,2,3,-trimethylheptane, cyclopentane, methylcyclopentane, cyclohexane, methylcyclohexane, decahydronaphthalene, and other saturated or aliphatic hydrocarbons; diethyl ether, isopropyl ether, isoamyl ether, tetrahydrofuran (THF), dioxane, tetrahydrofurfuryl alcohol, diethylene glycol, cyclo-

[Chemical Structure 8]

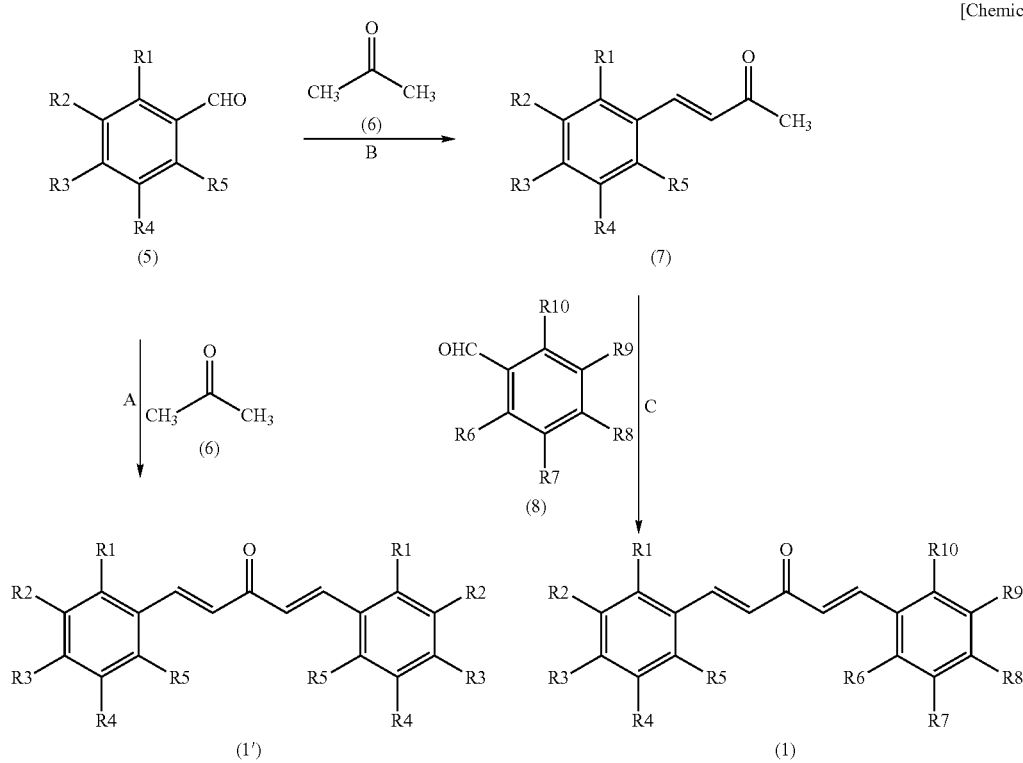

(wherein each group has the same meaning as given above).

The symmetrical bis(arylmethylidene)-acetone compound of General Formula (1') can be obtained by reacting acetone hexylmethyl ether, methylcellosolve, cellosolve, butylcellosolve, methyl-tert-butanol, and other ethers; methylethylketone, furfural, methylisobutylketone, mesityl oxide, diacetone alcohol, cyclohexanone, and other ketones; acetonitrile, benzonitrile, and other nitriles; dimethylsulfoxide (DMSO), sulfolane, and other sulfoxides; formamide, N,N-dimethylformamide (DMF), N,N,-dimethylacetamide, and other amides; methyl formate, ethyl formate, ethyl acetate, butyl acetate, methoxybutyl acetate, cellosolve acetate, diethyl carbonate, glycol carbonate, and other esters; formic acid, acetic acid, propionic acid, acetic anhydride, and other organic acids; hexamethylphosphotriamide, pyridine, quinoline, and other heterocyclic compounds; aniline, N-methylaniline, and other aromatic amines; and nitro compounds. The solvents can be used alone, or two or more types may be mixed together as necessary in ratios from, e.g., 1:1 to 1:10.

The reactions of the present invention can be preferably performed under basic conditions. Basic conditions can be attained using, e.g., aqueous solutions of sodium hydroxide, potassium hydroxide, ammonium hydroxide, sodium carbonate, potassium carbonate, sodium hydrogen carbonate, potassium hydrogen carbonate, or other bases. The amount of the base should be small relative to the amount of other compounds. Examples include amounts of 1/1.1 to 1/10,000, typically 1/5 to 1/5000, or, in other cases, 1/10 to 1/2000, 1/20 to 1/1000, or 1/50 to 1/500 relative to the amount of other compounds, but it shall be apparent that the appropriate amount can be selected according to the combination of starting compounds. The reaction temperature is usually –100° C. to 200° C., preferably –80° C. to 150° C., more preferably –10° C. to 100° C., and even more preferably 0° C. to 50° C., where 0° C. to room temperature is also acceptable. The reaction time is usually in the range of 1 minute to 2 weeks, preferably 5 minutes to 50 hours, more preferably 10 minutes to 35 hours, and even more preferably 15 minutes to 20 hours.

The reaction solution itself or the crude products may be used in subsequent reactions, but the products may also be isolated from the reaction mixture according to standard methods. The isolation and purification can be effected by adaptations of ordinary chemical operations including, for example, condensation, vacuum concentration, distillation, fractional distillation, solvent extraction, liquid conversion, solvent substitution, high performance liquid chromatography (HPLC), thin-layer chromatography (TLC), column chromatography, other chromatographic methods, crystallization, recrystallization, or other methods. Various isomers can be separated by conventional methods utilizing a difference of physico-chemical properties among such isomers. For example, stereochemically pure isomers can be obtained from racemic mixtures by an ordinary racemic resolution (e.g., by first converting said racemic mixtures with usual optically-active acids (including tartaric acid, etc.) to diastereomer salts followed by optical resolution, etc.). Diastereomers can be separated by ordinary methods such as selective crystallization or chromatographic techniques. Pure optically-active isomeric forms of the compounds of the present invention may also be obtained from the pure optically-active isomeric forms of the appropriate starting materials and intermediates.

As used herein, "the compound(s) of the present invention" may include salts thereof, hydrates and solvates thereof, a variety of prodrug forms derived from functional groups existing in compound molecules. The prodrugs of the compounds according to the present invention include those compounds which can be transformed in vivo, for example, by metabolic processes, including hydrolysis, oxidation, reduction, trans-esterification, and the like, to yield the parent compounds of the formula (1), etc. Representatives of such prodrugs are ester-, ether-, amide-, alcohol-, and amine-derivatives thereof. Preferred compounds according to the present invention are potently active in inhibiting the growth of cancer cells and in preventing carcinogenesis. Some of the compounds of the present invention may exist in more than one tautomeric form. This invention extends to all tautomeric forms. The compounds of the instant invention may also contain one or plural asymmetric carbon atoms and thus give rise to optical isomers such as (R)- and (S)-isomers, racemates, diastereoisomers, etc. The present invention includes all such possible isomers, and their racemic and resolved, enantiomerically pure forms, as well as all mixtures thereof. The compounds of the invention may be isolated in the form of hydrates, solvates with, for example, ethanol and the like, and a variety of crystalline substances. The compounds of General Formula (1) may be in a free form or a salt form. Such salts include those formed from any of medically or pharmaceutically utilizable non-toxic or low toxic inorganic or organic acids. Examples of the salts are metal salts, ammonium salts, salts with organic bases, salts with inorganic acids, salts with organic acids, and salts with basic or acidic amino acids.

The compounds of the present invention are useful as, e.g., agents for inhibiting the growth of cancer cells, anti-carcinogenic agents, anti-cancer agents (antineoplastic agents), and anti-tumor agents. Preferable examples of the active component for pharmaceutical drugs or other biologically active agents are bis(arylmethylidene)-acetone compounds or their salts, having the General Formula (4):

[Chemical Structure 9]

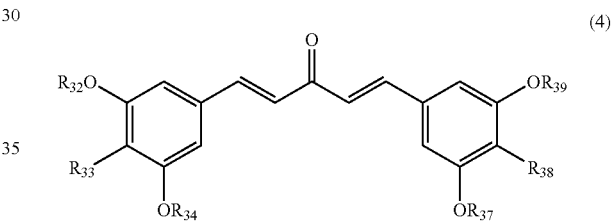

(4)

(wherein $R_{33}$ and $R_{38}$ may be the same or different and are each independently a member selected from the group consisting of a hydrogen atom, a halogen atom, a hydroxy group, a nitro group, an alkoxy group, an alkoxyalkoxy group, an alkoxyalkoxyalkoxy group, and an azido-alkoxy group, or $R_{33}$ may be taken together with the adjacent substituent $OR_{32}$ or $OR_{34}$ to form an alkylene-dioxy bridge, and/or $R_{38}$ may be taken together with the adjacent substituent $OR_{37}$ or $OR_{39}$ to form an alkylene-dioxy bridge; and $R_{32}$, $R_{34}$, $R_{37}$, and $R_{39}$ may be the same or different and are each independently a member selected from the group consisting of a hydrogen atom, an alkyl group, an alkoxyalkyl group, an alkoxyalkoxyalkyl group, and an azido-alkyl group, or may be taken together with the adjacent substituent $R_{33}$ or $R_{38}$ to form the aforementioned bridge). Examples of the aforementioned "alkyl group," "alkoxyalkyl group," "alkoxyalkoxyalkyl group," and "azido-alkyl group" include those corresponding to the groups described as the "alkoxy group," "alkoxyalkoxy group," "alkoxyalkoxyalkoxy group," and "azido-alkoxy group" in relation to Formula (1) above.

In the present invention, examples of compounds having the noted activities include (1E,4E)-(1,5-diphenyl)penta-1,4-dien-3-one (GO-Y012). (1E,4E)-1,5-bis-(4-methoxyphenyl) penta-1,4-dien-3-one (GO-Y013), (1E,4E)-1,5-bis-(2,3-dimethoxyphenyl)penta-1,4-dien-3-one (GO-Y015), (1E, 4E)-1,5-bis-(2-chlorophenyl)penta-1,4-dien-3-one (GO-Y017), (1E,4E)-1,5-bis-(4-bromophenyl)penta-1,4-dien-3-one (GO-Y018), (1E,4E)-1,5-bis-(2-methoxyphenyl)penta- 1,4-dien-3-one (GO-Y019), (1E,4E)-1,5-bis-(2,3,4-trimethoxyphenyl)penta-1,4-dien-3-one (GO-Y020), (1E,4E)-1,5-bis-(2,4,5-trimethoxyphenyl)penta-1,4-dien-3-one (GO-Y021), (1E,4E)-1,5-bis-(3-hydroxy-4-methoxyphenyl)penta-1,4-dien-3-one (GO-Y023), (1E,4E)-1,5-bis-(4-hydroxy-3,5-dimethoxyphenyl)penta-1,4-dien-3-one (GO-Y026), (1E,4E)-1,5-bis-(3,5-bismethoxymethoxyphenyl)penta-1,4-dien-3-one (GO-Y030, BBMMPP), (1E,4E)-1,5-bis-(3,5-dimethoxy-4-methoxymethoxyphenyl)penta-1,4-dien-3-one (GO-Y031. BDMMMPP), (1E,4E)-1,5-bis-(3-nitrophenyl)penta-1,4-dien-3-one (GO-Y035), (1E,4E)-1,5-bis-(3,5-dihydroxyphenyl)penta-1,4-dien-3-one (GO-Y038), (1E,4E)-1,5-bis-(3,5-dimethoxy-4-methoxyethoxymethoxyphenyl)penta-1,4-dien-3-one (GO-Y039), (1E,4E)-1,5-bis-(3,4-bismethoxymethoxyphenyl)penta-1,4-dien-3-one (GO-Y040), (1E,4E)-1,5-bis-[4-(2-hydroxyethoxy)-3,5-dimethoxyphenyl]penta-1,4-dien-3-one (GO-Y044), (1E,4E)-1-(3,4-dimethoxyphenyl)-5-(3,4,5-trimethoxyphenyl)penta-1,4-dien-3-one (GO-Y046), (1E,4E)-1-(3,4-dimethoxyphenyl)-5-(4-methoxyphenyl)penta-1,4-dien-3-one (GO-Y047), (1E,4E)-1,5-bis-(3,5-dimethoxy-4-prop-2-ynyloxyphenyl)penta-1,4-dien-3-one (GO-Y048), (1E,4E)-1-(4-methoxyphenyl)-5-(3,4,5-trimethoxyphenyl)penta-1,4-dien-3-one (GO-Y049), (1E,4E)-5-(3,4-dimethoxyphenyl)-1-(3-hydroxy-4-methoxyphenyl)penta-1,4-dien-3-one (GO-Y050), (1E,4E)-5-(3,4-dimethoxyphenyl)-1-(4-hydroxy-3-methoxy-phenyl)penta-1,4-dien-3-one (GO-Y051), (1E,4E)-5-(3,4-dimethoxyphenyl)-1-[3-(1-ethoxyethoxy)-4-methoxyphenyl]-penta-1,4-dien-3-one (GO-Y052), (1E,4E)-5-(3,4-dimethoxyphenyl)-1-[4-(1-ethoxyethoxy)-3-methoxyphenyl]-penta-1,4-dien-3-one (GO-Y053), (1E,4E)-1-(4-hydroxy-3-methoxyphenyl)-5-(3-methoxy-4-methoxymethoxyphenyl)penta-1,4-dien-3-one (GO-Y055), (1E,4E)-1-(3-hydroxy-4-methoxy-phenyl)-5-(3-methoxy-4-methoxymethoxyphenyl)penta-1,4-dien-3-one (GO-Y056), (1E,4E)-1-[3-(1-ethoxyethoxy)-4-methoxy-phenyl]-5-(3-methoxy-4-methoxymethoxyphenyl)penta-1,4-dien-3-one (GO-Y057), (1E,4E)-1-[4-(1-ethoxyethoxy)-3-methoxy-phenyl]-5-(3-methoxy-4-methoxymethoxyphenyl)penta-1,4-dien-3-one (GO-Y058), (1E,4E)-1-(3,5-dimethoxy-4-prop-2-ynyloxy-phenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxyphenyl)penta-1,4-dien-3-one (GO-Y062), (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063), (1E,4E)-1,5-bis-[4-(2-azidoethoxy)-3,5-dimethoxyphenyl]penta-1,4-dien-3-one (GO-Y065), (1E,4E)-1,5-bis-(3,5-dimethoxymethoxyphenyl)penta-1,4-dien-3-one (GO-Y067), and 1,5-bis(3,4,5-trimethoxyphenyl)penta-1,4-dien-3-one.

In the present invention, examples of compounds having preferable biological activities include (1E,4E)-(1,5-diphenyl)penta-1,4-dien-3-one (GO-Y012), (1E,4E)-1,5-bis-(3,4,5-trimethoxyphenyl)penta-1,4-dien-3-one (GO-Y016, BTMP), (1E,4E)-1,5-bis-(3-hydroxy-4-methoxyphenyl)penta-1,4-dien-3-one (GO-Y023), (1E,4E)-1,5-bis-(4-hydroxy-3,5-dimethoxyphenyl)penta-1,4-dien-3-one (GO-Y026), (1E,4E)-1,5-bis-(3,5-bismethoxymethoxyphenyl)penta-1,4-dien-3-one (GO-Y030, BBMMPP), (1E,4E)-1,5-bis-(3,5-dimethoxy-4-methoxymethoxyphenyl)penta-1,4-dien-3-one (GO-Y031, BDMMMPP), (1E,4E)-1,5-bis-(3,5-dimethoxy-4-methoxyethoxymethoxyphenyl)penta-1,4-dien-3-one (GO-Y039), (1E,4E)-1,5-bis-(3,4-bismethoxymethoxyphenyl)penta-1,4-dien-3-one (GO-Y040), (1E,4E)-1,5-bis-[4-(2-hydroxyethoxy)-3,5-dimethoxyphenyl]penta-1,4-dien-3-one (GO-Y044), (1E,4E)-1-(3,4-dimethoxyphenyl)-5-(3,4,5-trimethoxy-phenyl)penta-1,4-dien-3-one (GO-Y046), (1E,4E)-1,5-bis-(3,5-dimethoxy-4-prop-2-ynyloxyphenyl)penta-1,4-dien-3-one (GO-Y048), (1E,4E)-5-(3,4-dimethoxyphenyl)-1-(4-hydroxy-3-methoxyphenyl)penta-1,4-dien-3-one (GO-Y051), (1E,4E)-5-(3,4-dimethoxyphenyl)-1-[4-(1-ethoxyethoxy)-3-methoxy-phenyl]penta-1,4-dien-3-one (GO-Y053), (1E,4E)-1-(4-hydroxy-3-methoxyphenyl)-5-(3-methoxy-4-methoxymethoxy-phenyl)penta-1,4-dien-3-one (GO-Y055), (1E,4E)-1-(3-hydroxy-4-methoxyphenyl)-5-(3-methoxy-4-methoxymethoxy-phenyl)penta-1,4-dien-3-one (GO-Y056), (1E,4E)-1-[3-(1-ethoxyethoxy)-4-methoxyphenyl]-5-(3-methoxy-4-methoxy-methoxyphenyl)penta-1,4-dien-3-one (GO-Y057), (1E,4E)-1-[4-(1-ethoxyethoxy)-3-methoxyphenyl]-5-(3-methoxy-4-methoxy-methoxyphenyl)penta-1,4-dien-3-one (GO-Y058), (1E,4E)-1-(3,5-dimethoxy-4-prop-2-ynyloxyphenyl)-5-(3,4,5-trimethoxy-phenyl)penta-1,4-dien-3-one (GO-Y060), (1E,4E)-1-(3,5-bis-methoxymethoxyphenyl)-5-(3,5-dimethoxy-4-prop-2-ynyloxy-phenyl)penta-1,4-dien-3-one (GO-Y062), (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063), (1E,4E)-1,5-bis-[4-(2-azidoethoxy)-3,5-dimethoxyphenyl]penta-1,4-dien-3-one (GO-Y065), and (1E,4E)-1,5-bis-(3,5-dimethoxy-methoxyphenyl)penta-1,4-dien-3-one (GO-Y067).

Examples of compounds having particularly preferable biological activity in the present invention include (1E,4E)-1,5-bis-(3,4,5-trimethoxyphenyl)penta-1,4-dien-3-one (GO-Y016, BTMP), (1E,4E)-1,5-bis-(4-hydroxy-3,5-dimethoxyphenyl)penta-1,4-dien-3-one (GO-Y026), (1E,4E)-1,5-bis-(3,5-bismethoxymethoxyphenyl)penta-1,4-dien-3-one (GO-Y030, BBMMPP), (1E,4E)-1,5-bis-(3,5-dimethoxy-4-methoxy-methoxyphenyl)penta-1,4-dien-3-one (GO-Y031, BDMMMPP), (1E,4E)-1,5-bis-(3,5-dimethoxy-4-methoxyethoxymethoxy-phenyl)penta-1,4-dien-3-one (GO-Y039), (1E,4E)-1,5-bis-[4-(2-hydroxy-ethoxy)-3,5-dimethoxyphenyl]penta-1,4-dien-3-one (GO-Y044), (1E,4E)-1,5-bis-(3,5-dimethoxy-4-prop-2-ynyloxy-phenyl)penta-1,4-dien-3-one (GO-Y048), (1E,4E)-1-(3,5-dimethoxy-4-prop-2-ynyloxyphenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxyphenyl)penta-1,4-lien-3-one (GO-Y062), (1E,4E)-1,5-bis-[4-(2-azidoethoxy)-3,5-dimethoxyphenyl]penta-1,4-dien-3-one (GO-Y065), and (1E,4E)-1,5-bis-(3,5-dimethoxymethoxyphenyl)penta-1,4-dien-3-one (GO-Y067).

The cancers and tumors in the present invention are found in a variety of tissues and organs and also include cancer cells, tumor cells, which include malignant tumor cells, and the like that are found in the component cells of these tissues and/or organs. Examples include brain tumors (glioblastoma multiforme and the like), spinal tumors, maxillary sinus cancer, cancer of the pancreatic gland, gum cancer, tongue cancer, lip cancer, nasopharyngeal cancer, mesopharyngeal cancer, hypopharyngeal cancer, laryngeal cancer, thyroid cancer, parathyroid cancer, lung cancer, pleural tumors, cancerous peritonitis, cancerous pleuritis, esophageal cancer, stomach cancer, colon cancer, bile duct cancer, gallbladder cancer, pancreatic cancer, hepatic cancer, kidney cancer, bladder cancer, prostate cancer, penile cancer, testicular tumors, cancer of the adrenal glands, uterocervical cancer, endometrial cancer, vaginal cancer, vulvar cancer, ovarian cancer, ciliated epithelial cancer, malignant bone tumors, soft-tissue sarcomas, breast cancer, skin cancer, malignant melanomas, basal cell tumors, leukemia, myelofibrosis with myeloid metaplasia, malignant lymphoma tumors, Hodgkin's disease, plasmacytomas, and gliomas.

When the active components of the present invention (e.g., (a) bis(arylmethylidene)-acetone compounds of Formula (1) or salts thereof, or (b) bis(arylmethylidene)-acetone compounds of Formula (4) or salts thereof) are used as pharmaceutical agents or drugs, the active components can be administered alone or in the form of a pharmaceutical composition or preparation in admixture with any of various pharmacologically-acceptable additives. Preferably, it may be administered in the form of a convenient pharmaceutical composition or formulation suitable for oral, topical, parenteral application, or the like. Any of dosage forms (including those for inhalation and rectal administration) may be selected according to the intended goal.

The active components of the present invention can be used in combination with any of various drugs, including antitumor drugs (antineoplastic drugs), tumor metastasis-inhibitors, inhibitors for thrombogenesis, therapeutic drugs for joint destruction, analgesics, anti-inflammatory drugs, immunoregulators (or immunomodulators) and/or immunosuppressants, which can be employed as not being restricted to particular species as long as they serve effectively or advantageously. For instance, they can be optionally selected from those known in the art.

In the case of patients with diseases or with risks therefor, the compounds of the present invention may be administered alone or, preferably in a form of a drug containing a pharmaceutically acceptable excipient. The active compound is administered by an oral route or injection, or by inhalation or other topically applicable routes. In any of the administration routes, a component (hereinafter sometimes referred to as "pharmaceutical component") selected from known pharmaceutical excipients can be optionally used. Specifically, examples of known excipients are disclosed in, for example, (1) Iyakuhin Tenkabutsu Handbook ("Handbook of Pharmaceutical Excipients"), Maruzen Co. (1989); (2) Iyakuhin Tenkabutsu Jiten, First Edition ("Encyclopedia of Pharmaceutical Excipients, First Edition"), Yakuji Nippo, Ltd. (1994); (3) Iyakuhin Tenkabutsu Jiten Tsuiho, First Edition ("Encyclopedia of Pharmaceutical Excipients, Supplement, First Edition"), Yakuji Nippo, Ltd. (1995); and (4) Yakuzaigaku ["Pharmacology"], Fifth Revised Edition, Nankodo Co. (1997). The pharmaceutical component may be optionally selected from the known pharmaceutical excipients shown above depending on the administration route and application purpose of the drug. For example, when the drug is administered orally, any excipient can be used as long as the excipient can constitute an oral drug as a pharmaceutical component and achieve purposes of the present invention. Generally, the excipient is selected from known pharmaceutical components including for example fillers, binders, disintegrants, lubricants, and coating agents. Examples of the oral drug include tablets, capsules, granules, fine granules, powders, and syrups. The oral drugs include controlled-release system preparations wherein the in vivo release of the compound of the present invention which is contained as the active ingredient is controlled using any of known pharmaceutical ingredients (for example, rapid-release drug preparations, sustained-release drug preparations, etc.). The aforementioned oral drug may include enteric preparations. In some cases, it is rather preferable that the oral drugs are prepared in the form of such enteric preparations. Such enteric preparations include coated formulations and matrix formulations, wherein any of enteric coating agents is employed, said enteric coating agent being selected from cellulose phthalate, hydroxypropyl methylcellulose phthalate, and methyl methacrylate-methacrylic acid copolymers, etc., and capsule formulations having any of the enteric coating agents as an ingredient for their coat.

Embodiments of pharmaceutical ingredients as used for the aforementioned oral drugs are listed below but not limited to:

(1) Examples of fillers: lactose, starch (including corn starch), crystalline cellulose, microcrystalline cellulose, crystalline cellulose-carmellose sodium, dextrin, sucrose, glucose, mannitol, calcium carbonate, calcium phosphate, calcium sulfate, calcium silicate, Crosspovidone, dried yeast, soybean oil unsaponifiable fractions (2) Examples of binders: hydroxypropylcellulose (HPC), starch (including corn starch), gelatin, gum arabic, methylcellulose (MC), carboxymethylcellulose (CMC), polyvinylpyrrolidone (PVP), ethylcellulose (EC), glucose, and sucrose (3) Examples of disintegrants: starch (including corn starch), agar, gelatin, CMC-Na, CMC-Ca, crystalline cellulose, crystalline cellulose and carmellose sodium, HPC having a low degree of substitution, cross-povidone, calcium carbonate, sodium hydrogen carbonate (4) Examples of lubricants: magnesium stearate, hydrogenated vegetable oils, talc, macrogol, light anhydrous silicic acid (5) Examples of coating agents: sucrose, HPC, shellac, gelatin, glycerin, sorbitol, EC, HPC, hydroxypropyl methylcellulose (HPMC), PVP, cellulose acetate phthalate (CAP), hydroxypropyl methylcellulose phthalate (HPMCP), methyl methacrylate-methacrylic acid copolymers, titanium oxide For injection, the additives include pharmaceutical ingredients suitable for aqueous or non-aqueous injections. Usually, the additive is selected from conventional pharmaceutical ingredients such solubilizers, solution adjuvants, suspending agents, buffers, stabilizers and preservatives. In addition, it may be selected from conventional ingredients suitable for preparing powders for injection, which are used in solution or suspension when administered. Specific examples of solubilizers for injections include injection solvents, physiological saline solutions, Ringer's solutions, vegetable oils (e.g., olive oil, sesame oil, and soybean oil), ethanol, propylene glycol, polyethylene glycol, glycerin, N,N-dimethylacetamide, and N-methyl-2-pyrrolidone. Specific examples of solution adjuvants, suspending agents, buffers, stabilizers and preservatives in injections include polyoxyethylene hardened castor oil, ethylenediamine, benzyl alcohol, polysorbate 80, carmellose sodium, sodium hydroxide, sodium citrate, sodium acetate, potassium dihydrogen phosphate, sodium hydrogen sulfite, ascorbic acid, methyl paraoxybenzoate, propyl paraoxybenzoate, and chlorobutanol. Specific examples of pharmaceutical ingredients constituting powders for injections include glucose and sorbitol.

When administered topically, for example, via inhalation, etc., the aforementioned additives as used herein include any of pharmaceutical ingredients known in the art, such as solution adjuvants, stabilizers, buffers, suspending agents, emulsifying agents, and preservatives. Embodiments of inhalants include aerosols. Aerosol-producing techniques are any of types including a spraying type wherein active drug ingredients are packed together with propellants such as fluorocarbon alternatives into a sealed container and sprayed, and a nebulizer or atomizer type using a pressured gas, such as carbon dioxide and nitrogen, filled in a container different from that for active drug ingredients. Specific examples of pharmaceutical ingredients such as propellants, solubilizers, stabilizers, buffering agents, suspending agents, emulsifying agents, and preservatives, for the aforementioned aerosols include chlorine-free fluorinated hydrocarbons (e.g., 1,1,1,2-tetrafluoroethane (HFA-134a) and 1,1,1,2,3,3,3-heptafluoropropane (HFA-227)), alcohols, propylene glycol, polyethylene glycol, polysorbate 80, glycerin, egg-yolk lecithin, soy bean lecithin, α-tocopherol, ascorbic acid, benzalkonium chloride, chlorobutanol, etc. When the aforementioned nebulizer or atomizer types are employed, the pharmaceutical ingredients used may include water for injection, purified water, etc. Further, the inhalants may also be prepared in the form of not only sprays wherein any of the above-defined propellants is used, nebulizers or atomizers, but also powders. Such powder inhalants can be in any of forms similar to available powder inhalants in the art (e.g., INTAL (registered trademark) capsule and metered-dose inhaler: SPINHALER (registered trademark); for administering sodium cromoglicate (Cromolyn sodium)).

In addition to the aforementioned inhalants, the compounds of the present invention may be administered topically in the form of ointments, transdermic patches, solutions for external use, eyedrops, nose drops or suppositories. Such topical pharmaceutical preparations may suitably contain pharmaceutical ingredients as disclosed in the aforementioned "Iyakuhin Tenkabutsu Handbook (Handbook of PHARMACEUTICAL EXCIPIENTS)", "Iyakuhin Tenkabutsu Jiten (Pharmaceutical Excipient Dictionary)", etc. Desired oral drugs, injections or drugs for topical applications (including inhalants) comprising the compound of the present invention in admixture with the aforementioned ingredient can be prepared according to manufacturing methods known per se, for example, those described in The 15th Pharmacopoeia of Japan (JPXV) or appropriately modified ones. The pharmaceutical compositions (drugs) of the present invention are administered to mammals, particularly including human. The doses of these compounds or salts thereof are usually about 0.1 to 1,000 mg (per day), preferably about 0.1 to 500 mg (per day) for oral administration; usually about 0.01 to 200 mg (per day), preferably about 0.05 to 100 mg (per day) for injection; and usually about 0.01 to 200 mg (per day), preferably about 0.05 to 100 mg (per day) for topical applications. Specific administration routes and dose levels (including the optimal dose) for any particular patient will be employed depending upon a variety of factors including the patient's conditions (general health, the severity of the particular disease or symptom undergoing therapy, the presence or absence of complications thereof, etc.), the age, sex, body weight, and the like.

Details of the present invention are described by the following examples, but such examples are provided only for illustrative purposes, and for referential embodiments of the present invention. These examples should in no way be construed as limiting and restricting the scope of the invention disclosed herein. It should be understood in the present invention that a variety of embodiments can be made or executed within the spirit, scope and concept disclosed herein. All the examples were implemented or can be performed, unless otherwise disclosed herein specifically, according to standardized techniques which are well-known and conventional to those skilled in the art.

EXAMPLE 1

Step A

Symmetric compounds can be obtained by the action of acetone and an aryl aldehyde (1:2) in an aqueous solution of ethanol and 10% sodium hydroxide at room temperature. When the solubility of the aryl aldehyde in ethanol is exceptionally poor, the aryl aldehyde can be dissolved by using a small amount of tetrahydrofuran. When the aryl aldehyde has hydroxyl substituent groups, the reaction is performed after properly protecting these groups using ethoxyethyl, tetrahydropyran, methoxymethyl, or other groups. The products are stable under general conditions for deprotecting these groups.

Step B

A methyl ketone compound that is an intermediate of an asymmetric compound can be obtained using the acetone and aryl aldehyde of Step A in a 4:1 ratio.

Step C

An asymmetric compound can be obtained using the methyl ketone compound and an aryl aldehyde in a 1:1 ratio under the conditions of Mixture 1.

Synthesis of methyl (4-formyl-2,6-dimethoxyphenoxy)-acetate

To a solution of syringaldehyde (3.0 g, 16.5 mmol) in methylene chloride (33 mL, 0.5 M) was added Hunig's base (5.7 mL, 32.7 mmol) and methyl bromoacetate (1.87 mL, 19.8 mmol), and the mixture was stirred for 15 hours at room temperature, followed by addition of $H_2O$. The reaction mixture was then extracted with chloroform, washed with saturated saline, next dried over magnesium sulfate, and evaporated under diminished pressure. The residue was subjected to silica gel chromatography, and a white solid product (3.895 g, 92.9%) was obtained from an ethyl acetate/hexane eluent (1:1.5 v/v). Recrystallization of a portion of the white solid product from ethyl acetate gave a colorless needle-like crystal (m.p. 100 to 102° C.).

Synthesis of 2-(4-hydroxymethyl-2,6-dimethoxyphenoxy)-ethanol

To a solution of (4-formyl-2,6-dimethoxyphenoxy)-acetate methyl ester (1.5 g, 5.9 mmol) in THF (30 mL, 0.2 M) was added $LiAlH_4$ (403 mg, 10.6 mmol) at water temperature. The reaction mixture was stirred for 6 hours at room temperature, followed by addition of $H_2O$, and then subjected to celite filtration. Evaporation of the resultant mixture under diminished pressure gave a white solid. Recrystallization of this solid from chloroform/hexane gave a colorless needle-like crystal (1.346 g, 100%, m.p. 26 to 28° C.).

Synthesis of 4-(2-hydroxyethoxy)-3,5-dimethoxy-benzaldehyde

To a solution of 2-(4-hydroxymethyl-2,6-dimethoxyphenoxy)ethanol (1.78 g, 7.8 mmol) in methylene chloride (39 mL, 0.2 M) was added $MnO_2$ (6.8 g, 78 mmol). The reaction mixture was stirred for 3 hours at room temperature, then subjected to celite filtration, and evaporated under reduced pressure. Recrystallization of the residue from diethyl ether gave a colorless granular crystal (1.586 g, 89.8%, m.p. 69 to 70° C.).

Synthesis of 4-[2-(1-ethoxyethoxy)-ethoxy]-3,5-dimethoxybenzaldehyde

To a solution of 4-(2-hydroxyethoxy)-3,5-dimethoxybenzaldehyde (1.5 g, 6.6 mmol) in methylene chloride (22 mL, 0.3 M) was added ethyl vinyl ether (3.4 mL, 19.9 mmol). After addition of PPTS (168 mg, 0.66 mmol), the reaction mixture was stirred for 40 minutes at room temperature. An aqueous saturated sodium hydrogen carbonate solution was added to the reaction fluid, which was then extracted with ethyl acetate, washed with saturated saline, dried over magnesium sulfate, and evaporated under reduced pressure to afford a residue containing an ethoxyethyl-protected 4-(2-hydroxyethoxy-3,5-dimethoxybenzaldehyde.

Synthesis of 1,5-bis-[4-[2-(1-ethoxyethoxy)-ethoxy]-3,5-dimethoxy-phenyl]-penta-1,4-dien-3-one To an aqueous 10% sodium hydroxide solution (6.0 mL, 1.0 M) was added slowly dropwise a mixture of an ethanol (4.0 mL, 1.5 M) solution of a residue (1.8 g, approximately 6.0 mmol) containing 4-[2-(1-ethoxyethoxy)-ethoxy]-3,5-dimethoxybenzaldehyde and acetone (230 μL, 3.1 mmol), and the resultant mixture was stirred for 6 hours at room temperature, followed by addition of 10% hydrochloric acid. The mixture was then extracted with ethyl acetate, washed with saturated saline, dried over magnesium sulfate, and evaporated under reduced pressure to give a residue containing an ethoxyethyl-protected GO-Y044.

Synthesis of (1E,4E)-1,5-bis-[4-(2-hydroxyethoxy)-3,5-dimethoxyphenyl]penta-1,4-dien-3-one (GO-Y044)

To a solution of a residue containing ethoxyethyl-protected GO-Y044 in THF (8 mL) was added an aqueous 1% hydrochloric acid solution (8 mL), and the resultant mixture was stirred for 30 minutes at room temperature, admixed with an aqueous saturated sodium hydrogen carbonate solution, extracted with ethyl acetate, and washed with saturated saline, dried over magnesium sulfate, and evaporated under reduced pressure. The residue was subjected to silica gel chromatography. The resulting yellow oil from an ethyl acetate/hexane eluent (1:6 v/v) was subjected to molecular sieve chromatography to afford a yellow solid GO-Y044 (127.8 mg, 8.1% for the two steps). Recrystallization of a portion of the yellow solid product from ethanol gave a yellow granular crystal.

EXAMPLE 2

Synthesis of (3E)-4-(3,5-dimethoxy-4-prop-2-ynyloxy-phenyl)-but-3-en-2-one

To an aqueous 10% sodium hydroxide solution (4.3 mL, 1.0 M) was added slowly dropwise a mixture of an ethanol (4.3 mL, 1.0 M) solution of 3,5-dimethoxy-4-prop-2-ynyloxybenzaldehyde (0.95 g, 4.3 mmol) and acetone (1.27 mL, 17.3 mmol), and the resultant mixture was stirred for 1 hour at room temperature, followed by addition of 10% hydrochloric acid. The mixture was then extracted with ethyl acetate, washed with saturated saline, dried over magnesium sulfate, and evaporated under reduced pressure to give a residue which was subjected to silica gel chromatography. A white solid (605 mg, 54%) was obtained from an ethyl acetate/hexane eluent (1:1 v/v).

Synthesis of (1E,4E)-1-(3,5-dimethoxy-4-methoxymethoxyphenyl)-5-(3,5-dimethoxy-4-prop-2-ynyloxy-phenyl)penta-1,4-dien-3-one (GO-Y063)

To an aqueous 10% sodium hydroxide solution (0.384 mL, 1.0 M) was added slowly dropwise an ethanol (0.384 mL, 1.0 M)-tetrahydrofuran (2.0 mL, 0.26 M) solution of 3,5-dimethoxy-4-methoxymethoxybenzaldehyde (87 mg, 0.384 mmol) and methyl ketone (100 mg, 0.384 mmol), and the resulting mixture was stirred for 5 hours at room temperature, admixed with 10% hydrochloric acid, extracted with ethyl acetate, washed with saturated saline, then dried over magnesium sulfate, and evaporated under reduced pressure to give a residue which was subjected to silica gel chromatography. Yellow solid GO-Y063 (54 mg, 30%) was obtained from an ethyl acetate/hexane eluent (1:1 v/v).

EXAMPLE 3

The compounds below were synthesized in the same manner as Examples 1 and 2.

(1) (1E,4E)-1,5-bis-(3,4-bismethoxymethoxyphenyl) penta-1,4-dien-3-one (GO-Y035)

Yellow crystals (MeOH): mp 86 to 88° C.; IR(CHCl$_3$) 1646, 1618 cm$^{-1}$; $^1$H-NMR (400 MHz, CDCl$_3$) δ 7.69 (2H, d, J=15.9 Hz) 7.21 (2H, dd, J=8.2, 1.7 Hz), 7.15 (2H, d, J=1.69 Hz), 6.96 (2H, d, J=15.9 Hz), 6.90 (2H, d, J=8.2 Hz), 3.95 (6H, s) 3.93 (6H, s); $^{13}$C-NMR (100 Hz, CDCl$_3$) δ 188.0, 175.0, 148.6, 142.4, 135.0, 127.3, 123.1, 122.5, 110.7, 109.5, 72.8, 55.8, 55.7; MS m/z 354 (M$^+$, 100%); HRMS calcd for C$_{21}$H$_{22}$O$_5$ 354.1467. found 354.1460.

(2) (1E,4E)-1,5-bis-benzo[1,3]dioxol-5-yl-penta-1,4-dien-3-one (GO-949)

$^1$H-NMR (400 MHz CDCl$_3$) δ=7.64 (2H, d, J=16.0 Hz), 7.12 (2H, d, J=1.7 Hz), 7.09 (2H, dd, J=8.0, 1.7 Hz), 6.88 (2H, d, J=15.7 Hz), 6.83 (2H, d, J=8.0 Hz), 6.02 (4H, s).

(3) (1E,4E)-1,5-dinaphthalen-2-yl-penta-1,4-dien-3-one (GO-Y011)

Pale yellow powder (xylene), mp=244 to 246° C.; IR (CHCl$_3$): 1648 cm$^{-1}$; $^1$H-NMR (400 MHz, CDCl$_3$) δ=8.05 (2H, s), 7.94 (2H, d, J=15.9 Hz), 7.89 to 7.84 (6H, m), 7.78 (2H, d, J=8.7 Hz), 7.55 to 7.52 (4H, m), 7.24 (2H, d, J=15.9 Hz); MS m/z 334 (M$^+$); HRMS Calcd C$_{25}$H$_{18}$O: 334.1358. Found: 334.1355.

(4) (1E,4E)-1,5-diphenyl-pentadien-3-one (GO-Y012)

Yellow plates (Et$_2$O): mp 105 to 107° C.; IR (CHCl$_3$) 1651, 1626 cm$^{-1}$; $^1$H-NMR (400 MHz, CDCl$_3$) δ 7.74 (2H, d, J=15.9 Hz), 7.61 (4H, m), 7.42 (6H, m), 7.09 (2H, d, J=15.9 Hz); $^{13}$C-NMR (100 Hz, CDCl$_3$) δ 188.9, 143.3, 134.8, 130.5, 128.9, 128.4, 125.4; MS m/z 234 (M$^+$, 100%); HRMS calcd for C$_{17}$H$_{14}$O 234.1045, found 234.1024.

(5) (1E,4E)-1,5-bis-(4-methoxyphenyl)penta-1,4-dien-3-one (GO-Y013)

Yellow plates (Et$_2$O): mp 130 to 132° C.; IR (CHCl$_3$) 1652, 1630 cm$^{-1}$; $^1$H-NMR (400 MHz, CDCl$_3$) δ 7.69 (2H, d, J=15.7 Hz), 7.56 (4H, d, J=8.5 Hz), 6.95 (2H, d, J=15.7 Hz), 6.92 (4H, d, J=8.5 Hz), 3.85 (6H, s); $^{13}$C-NMR (100 Hz, CDCl$_3$) δ 188.7, 161.4, 142.5, 130.0, 127.5, 123.4, 114.3, 55.2; MS m/z 294 (M$^+$, 100%); HRMS calcd for C$_{19}$H$_{18}$O$_3$ 294.1256. found 294.1248.

(6) (1E,4E)-1,5-bis-(2,3-dimethoxyphenyl)penta-1,4-dien-3-one (GO-Y015)

Yellow plates (Et$_2$O): mp 134 to 136° C.; IR (CHCl$_3$) 1650, 1617 cm$^{-1}$; $^1$H-NMR (400 MHz, CDCl$_3$) δ 8.03 (2H, d, J=16.2 Hz), 7.26 (2H, dd, J=8.3, 0.8 Hz), 7.15 (2H, d, J=16.2 Hz), 7.09 (2H, t, J=8.1 Hz), 6.96 (2H, dd, J=8.3, 0.8 Hz), 3.90 (6H, s), 3.89 (6H, s); $^{13}$C-NMR (100 Hz, CDCl$_3$) δ 189.7, 153.7, 148.8, 137.9, 129.1, 126.9, 124.2, 119.5, 114.1, 61.4, 55.9; MS m/z 323 (M$^+$), 323 (100%);
HRMS calcd for C$_{21}$H$_{22}$O$_5$ 354.1467. found 354.1464.

(7) (1E,4E)-1,5-bis-(3,4,5-trimethoxyphenyl)penta-1,4-dien-3-one (GO-Y016)

Yellow plates (CHCl$_3$-MeOH): mp 123 to 124° C.; IR (CHCl$_3$): 1649, 1617, 1581 cm$^{-1}$; $^1$H-NMR (400 MHz, CDCl$_3$) δ 7.66 (2H, d, J=15.9 Hz), 6.98 (2H, d, J=15.9 Hz), 6.85 (2H, s), 3.92 (12H, s), 3.90 (6H, s); $^{13}$C-NMR (100 Hz, CDCl$_3$) δ 176.9, 153.5, 143.3, 130.3, 124.8, 105.7, 61.0, 56.2; MS m/z 414 (M$^+$), 181 (100%); FIRMS calcd for C$_{23}$H$_{26}$O$_7$ 414.1679. found 414.1668.

(8) (1E,4E)-1,5-bis-(2-chlorophenyl)penta-1,4-dien-3-one (GO-Y017)

Yellow plates (Et$_2$O): mp 116 to 118° C.; IR (CHCl$_3$) 1671, 1617 cm$^{-1}$; $^1$H-NMR (400 MHz, CDCl$_3$) δ 8.13 (214, d, J=16.2 Hz), 7.72 (214, dd, J=6.5, 2.9 Hz), 7.44 (2H, dd, J=7.2, 2.2 Hz), 7.32 (4H, m), 7.06 (2H, d, J=16.2 Hz); $^{13}$C-NMR (100 Hz, CDCl$_3$) δ 188.7, 139.3, 135.4, 133.0, 131.2, 130.2, 127.7, 127.5, 127.1; MS m/z 302 (M$^+$), 267 (100%); HRMS calcd for C$_{17}$H$_{12}$Cl$_2$O 302.0265, found 302.0227.

(9) (1E,4E)-1,5-bis-(4-bromophenyl)penta-1,4-dien-3-one (GO-Y018)

Yellow needles (CHCl$_3$-MeOH): mp 211 to 213° C.; IR (CHCl$_3$) 1653, 1621 cm$^{-1}$; $^1$H-1-NMR (400 MHz, CDCl$_3$) δ 7.67 (2H, d, J=15.9 Hz), 7.55 (4H, d, J=8.5 Hz), 7.47 (4H, d, J=8.5 Hz), 7.04 (2H, d, J=15.9 Hz); $^{13}$C-NMR (100 Hz, CDCl$_3$) δ 142.1, 139.6, 133.6, 132.3, 129.7, 125.8; MS m/z 389 (M$^+$), 102 (100%); HRMS calcd for C$_{17}$R$_{12}$Br$_2$O$_6$ 389.9255. found 389.9210.

(10) (1E,4E)-1,5-bis-(2-methoxyphenyl)penta-1,4-dien-3-one (GO-Y019)

Yellow plates (CHCl$_3$-MeOH): mp 124 to 126° C.; IR (CHCl$_3$) 1645, 1612 cm$^{-1}$; $^1$H-NMR (400 MHz, CDCl$_3$) δ 8.07 (2H, d, J=16.2 Hz), 7.63 (2H, dd, J=7.7, 1.4 Hz), 7.37 (2H, td, J=7.6, 1.3 Hz), 7.18 (2H, d, J=16.2 Hz), 6.99 (2H, t, J=7.5 Hz), 6.94 (2H, d, J=8.2 Hz), 3.92 (6H, s); $^{13}$C-NMR (100 Hz, CDCl$_3$) δ 190.0, 158.6, 138.2, 131.5, 128.7, 126.3, 124.0, 120.7, 111.2, 55.5; MS m/z 294 (M$^+$), 263 (100%); HRMS calcd for C$_{19}$H$_{18}$O$_3$ 294.1256. found 294.1248.

(11) (1E,4E)-1,5-bis-(2,3,4-trimethoxyphenyl)penta-1,4-dien-3-one (GO-Y020)

Yellow plates (MeOH): $^1$H-NMR (400 MHz, CDCl$_3$) δ 7.92 (2H, d, J=16.1 Hz), 7.34 (2H, d, J=8.8 Hz), 7.08 (2H, d, J=16.1 Hz), 6.72 (2H, d, J=8.8 Hz), 3.95 (6H, s), 3.91 (6H, s), 3.89 (6H, s); MS m/z 414 (M$^+$); HRMS calcd for C$_{23}$H$_{26}$O$_7$ 414.1679.

(12) (1E,4E)-1,5,-bis-(2,4,5-trimethoxyphenyl)penta-1,4-dien-3-one (GO-Y021)

Yellow plates (MeOH): mp 166 to 168° C.; IR (CHCl$_3$) 1639 cm$^{-1}$; $^1$H-NMR (400 MHz, CDCl$_3$) δ 8.04 (2H, d, J=16.1 Hz), 7.13 (2H, s), 7.03 (2H, d, J=15.9 Hz), 6.52 (2H, s), 3.95 (6H, s), 3.91 (6H, s), 3.90 (6H, s); $^{13}$C-NMR (100 Hz, CDCl$_3$) δ 189.6, 154.3, 152.3, 143.3, 143.3, 137.5, 124.0, 115.7, 111.0, 96.9, 56.5, 56.4, 56.1; MS m/z 414 (M$^+$), 383 (100%); HRMS calcd for C$_{23}$H$_{26}$O$_7$ 414.1679, found 414.1664.

(13) (1E,4E)-1,5-bis-(4-hydroxy-3-methoxyphenyl)penta-1,4-dien-3-one (GO-Y022)

Yellow crystals (MeOH): mp 68 to 70° C.; IR (CHCl$_3$) 3389, 1639 cm$^{-1}$; $^1$H-NMR (400 MHz, DMSO-d$_6$) δ 9.65 (2H, s), 7.64 (2H, d, J=15.9 Hz), 7.36 (2H, s), 7.19 (2H, d, J=8.2 Hz), 7.14 (2H, d, J=15.9 Hz), 6.82 (2H, d, J=8.2 Hz), 3.84 (6H, s); $^{13}$C-NMR (100 Hz, DMSO-d$_6$) δ 188.0, 149.4, 148.0, 142.7, 126.3, 123.3, 123.0, 115.7, 111.4, 55.7; MS m/z 326 (M$^+$, 100%); HRMS calcd for O$_{19}$H$_{18}$O$_5$ 326.1154, found 326.1139.

(14) (1E,4E)-1,5-bis-(3-hydroxy-4-methoxyphenyl)penta-1,4-dien-3-one (GO-Y023)

Yellow crystals (MeOH): mp 195 to 197° C.; IR (CHCl$_3$): 3431, 1681 cm$^{-1}$; $^1$H-NMR (400 MHz, CDCl$_3$) δ 7.64 (2H, d, J=15.8 Hz), 7.24 (2H, s), 7.12 (2H, d, J=8.3 Hz), 6.93 (2H, d, J=15.8 Hz), 6.87 (2H, d, J=8.3 Hz), 5.65 (2H, s), 3.95 (6H, s); $^{13}$C-NMR (100 Hz, CDCl$_3$) δ 148.6, 146.0, 142.8, 128.6, 124.0, 122.5, 114.9, 113.0, 110.6, 56.0; MS m/z 326 (M$^+$), 137 (100%); HRMS calcd for C$_{19}$H$_{18}$O$_5$ 326.1154, found 326.1139.

(15) (1E,4E)-1,5-bis-(4-hydroxy-3,5-dimethoxyphenyl)penta-1,4-dien-3-one (GO-Y026)

Yellow crystals (MeOH): mp 166 to 168° C.; IR (CHCl$_3$) 3399, 1605, 1509 cm$^{-1}$; $^1$H-NMR (400 MHz, CDCl$_3$) δ 7.66 (2H, d, J=15.8 Hz), 6.94 (2H, d, J=15.8 Hz), 6.87 (4H, s), 5.82 (2H, s), 3.95 (12H, s); $^{13}$C-NMR (100 Hz, CDCl$_3$) δ 188.4, 147.2, 143.4, 137.3, 126.3, 123.6, 105.4, 56.4; MS m/z 386 (M$^+$, 100%); HRMR calcd for C$_{21}$H$_{22}$O$_7$ 386.1366, found 386.1366.

(16) (1E,4E)-1,5-bis-(3,5-bismethoxymethoxyphenyl)penta-1,4-dien-3-one (GO-Y030)

Yellow needles (CHCl$_3$-Et$_2$O-hexane): mp 90 to 92° C.; IR (CHCl$_3$) 1654, 1626 cm$^{-1}$; $^1$H-NMR (400 MHz, CDCl$_3$) δ 7.63 (2H, d, J=15.8 Hz), 7.02 (21-1, d, J=15.8 Hz), 6.96 (4H, s), 6.79 (2H, s), 5.19 (8H, s), 3.50 (12H, s); $^{13}$C-NMR (100 Hz, CDCl$_3$) δ 188.8, 158.7, 143.1, 136.9, 126.0, 109.6, 107.2, 94.6, 56.1; MS m/z 474 (M$^+$), 474 (100%); HRMR calcd for C$_{25}$H$_{30}$O$_9$ 474.1890, found 474.1887.

(17) (1E,4E)-1,5-bis-(3,5-dimethoxy-4-methoxymethoxyphenyl)penta-1,4-dien-3-one (GO-Y031)

Yellow crystals (AcOEt): mp 146 to 148° C.; IR (CHCl$_3$) 1649, 1619 cm$^{-1}$; $^1$H-NMR (300 MHz, CDCl$_3$) δ 7.67 (2H, d, J=16.0 Hz), 6.98 (2H, d, J=16.0 Hz), 6.86 (4H, s), 5.18 (4H, s), 3.91 (12H, s), 3.61 (6H, s); $^{13}$C-NMR (100 Hz, CDCl$_3$) δ

188.3, 153.4, 143.2, 136.7, 130.6, 124.7, 105.4, 98.1, 57.2, 56.1; MS m/z 474 (M$^+$, 100%); HRMS calcd for $C_{25}H_{30}O_9$ 474.1890, found 474.1889.

(18) (1E,4E)-1,5-bis-(3-bromo-5-methoxyphenyl)penta-1,4-dien-3-one (GO-033)

Yellow plates (Et$_2$O): mp 181 to 183° C.; IR (CHCl$_3$) 1649, 1618 cm$^{-1}$; $^1$H-NMR (400 MHz, CDCl$_3$) δ 7.85 (2H, d, J=2.0 Hz), 7.62 (2H, d, J=15.9 Hz), 7.51 (2H, dd, J=8.3, 2.0 Hz), 6.93 (2H, d, J=15.9 Hz), 6.92 (2H, d, J=8.3 Hz), 3.95 (6H, s); $^{13}$C-NMR (100 Hz, CDCl$_3$) δ 188.0, 157.5, 141.3, 132.6, 129.5, 128.8, 124.3, 112.3, 111.8, 56.4; MS m/Z 452 (M$^+$, 100%); HRMR calcd for $C_{19}H_{16}Br_2O_3$ 449.1365, found 449.9441. Anal. Calcd for: $C_{19}H_{16}Br_2O_3$: C, 50.47; H, 3.57. Found: C, 50.46; H, 3.54.

(19) (1E,4E)-1,5-bis-(3-nitrophenyl)penta-1,4-dien-3-one (GO-Y035)

Pale yellow powder; $^1$H-NMR (400 MHz, CDCl$_3$) δ=8.51 (2H, s), 8.27 (2H, d, J=7.3 Hz), 7.91 (2H, d, J=7.5 Hz), 7.80 (2H, d, J=16.1 Hz), 7.63 (2H, dd, J=7.9, 7.9 Hz), 7.20 (2H, d, J=16.1 Hz); MS m/z 324 (M$^+$); HRMS Calcd $C_{17}H_{12}N_2O_5$: 324.0746. Found: 324.0729.

(20) (1E,4E)-1,5-bis-(3,5-dihydroxyphenyl)penta-1,4-dien-3-one (GO-Y038)

Yellow crystals (EtOH-H$_2$O): mp 298 to 300° C. (dec.); IR (CHCl$_3$): 3289, 1599 cm$^{-1}$; $^1$H-NMR (400 MHz, CD$_3$OD) δ 7.58 (2H, d, J=15.9 Hz), 7.07 (2H, d, J=15.9 Hz), 6.61 (4H, d, J=2.2 Hz), 6.34 (2H, t, J=2.2 Hz), 4.87 (4H, s); $^{13}$C-NMR (100 Hz, CD$_3$OD) δ 191.4, 160.0, 145.4, 137.8, 126.0, 107.9, 106.2; MS m/z 298 (M$^+$), 163 (100%); HRMR calcd for $O_{17}H_{14}O_5$ 298.0841, found 298.0860.

(21) (1E,4E)-1,5-bis-(3,5-dimethoxy-4-methoxyethoxymethoxyphenyl)penta-1,4-dien-3-one (GO-Y039)

Yellow crystals (Et$_2$O-hexane), mp 61 to 63° C.; IR (CHCl$_3$) 1649, 1617 1584 cm$^{-1}$; $^1$H-NMR (400 MHz, CDCl$_3$) δ 7.65 (2H, d, J=15.9 Hz), 6.97 (2H, d, J=15.9 Hz), 6.83 (4H), 5.25 (4H, s), 4.00 (4H, t, J=4.6 Hz), 3.88 (12H, s), 3.57 (4H, t, J=4.6 Hz), 3.37 (6H, s); $^{13}$C-NMR (100 Hz, CDCl$_3$) δ 188.3, 153.4, 143.2, 136.6, 130.6, 124.7, 105.3, 96.9, 71.6, 68.5, 59.0, 56.0; MS m/z 562 (M$^+$), 59 (100%); HRMR calcd for $C_{29}H_{38}O_{11}$ 562.2414, found 562.2414.

(22) (1E,4E)-1,5-bis-(3,4-bismethoxymethoxyphenyl)penta-1,4-dien-3-one (GO-Y040)

Yellow crystals (CHCl$_3$-Et$_2$O-hexane): nip 100 to 101° C.; IR (CHCl$_3$) 1649, 1618 cm$^{-1}$; $^1$H-NMR (400 MHz, CDCl$_3$) δ 7.66 (2H, d, J=15.9 Hz), 7.46 (2H, d, J=2.0 Hz), 7.24 (2H, dd, J=8.5, 2.0 Hz), 7.18 (2H, d, J=8.5 Hz), 6.95 (2H, d, J=15.9 Hz), 5.29 (4H, s), 5.29 (4H, s), 3.56 (6H, s), 3.53 (6H, s); $^{13}$C-NMR (100 Hz, CDCl$_3$) δ 188.5, 149.2, 147.3, 142.6, 129.2, 124.2, 123.9, 116.0, 115.6, 95.4, 95.0, 56.4, 56.3; MS m/z 474 (M$^+$, 45 (100%); HRMR calcd for $C_{25}H_{30}O_9$ 474.1890, found: 474.1886. Anal. Calcd for $C_{25}H_{30}O_9$: C, 63.28; H, 6.37. Found: C, 63.06; H, 6.45.

(23) (1E,4E)-1,5-bis-[4-(2-hydroxyethoxy)-3,5-dimethoxyphenyl]penta-1,4-dien-3-one (GO-Y044)

Yellow crystals (EtOH): mp 133 to 135° C.; IR (CHCl$_3$) 3431, 1681 cm$^{-1}$; $^1$H-NMR (400 MHz, CDCl$_3$) δ 7.65 (2H, d, J=15.9 Hz), 6.98 (211, d, J=15.9 Hz), 6.85 (4H, s), 4.17 (4H, m), 3.91 (12H, s), 3.75 (4H, m), 3.41 (2H, brs); $^{13}$C-NMR (100 Hz, CDCl$_3$) δ 189.1, 154.1, 143.8, 139.2, 131.2, 125.5, 105.9, 75.9, 61.7, 56.5; MS m/z 474 (M$^+$), 211 (100%); HRMR calcd for $C_{25}H_{30}O_9$ 474.1890, found 474.1898.

(24) (1E,4E)-1-(3,4-dimethoxyphenyl)-5-(3,4,5-trimethoxyphenyl)penta-1,4-dien-3-one (GO-Y046)

Yellow oil: IR (CHCl$_3$) 1647 cm$^{-1}$; $^1$H-NMR (400 MHz, CDCl$_3$) δ 7.70 (1H, d, J=15.7 Hz), 7.65 (1H, d, J=15.7 Hz). 7.21 (1H, dd, J=8.5, 1.9 Hz), 7.15 (1H, d, J=1.9 Hz), 6.98 (1H, d, J=15.7 Hz), 6.96 (1H, d, J=15.7 Hz), 6.90 (1H, d, J=8.2 Hz), 6.85 (2H, s), 3.95 (3H, s), 3.93 (3H, s), 3.92 (6H, s), 3.90 (3H, s); $^{13}$C-NMR (100 Hz, CDCl$_3$) δ 188.5, 153.4, 151.4, 149.3, 143.3, 142.9, 140.3, 130.3, 127.8, 124.9, 123.4, 123.1, 111.1 110.0, 105.6, 60.9, 56.2, 56.0, 55.9; MS m/z 384 (M$^+$), 384 (100%); HRMR calcd for $C_{22}H_{24}O_6$ 384.1573, found: 384.1563.

(25) (1E,4E)-1-(3,4-dimethoxyphenyl)-5-(4-methoxyphenyl)penta-1,4-dien-3-one (GO-Y047)

Yellow oil: IR (CHCl$_3$) 1646 cm$^{-1}$; $^1$H-NMR (400 MHz, CDCl$_3$) δ 7.70 (1H, d, J=15.8 Hz), 7.68 (1H, d, J=15.8 Hz), 7.57 (2H, d, J=8.5 Hz), 7.19 (1H, dd, J=8.3, 2.0 Hz), 7.13 (1H, d, J=2.0 Hz), 6.97 (1H, d, J=15.9 Hz), 6.94 (1H, d, J=15.9 Hz), 6.93 (2H, d, J=8.8 Hz), 6.88 (1H, d, J=8.3 Hz), 3.94 (3H, s), 3.93 (3H, s), 3.85 (3H, s); $^{13}$C-NMR (100 Hz, CDCl$_3$) δ 188.6, 161.4, 151.1, 149.1, 142.8, 142.6, 130.0, 127.8, 123.8, 123.1, 123.0, 114.3, 111.0, 109.7, 56.0, 55.9, 55.4; MS m/z 324 (M$^+$), 324 (100%); HRMR calcd for $C_{20}H_{20}O_4$ 324.1362, found: 324.1342.

(26) (1E,4E)-1,5-bis-(3,5-dimethoxy-4-prop-2-ynyloxyphenyl)penta-1,4-dien-3-one (GO-Y048)

Yellow plates (AcOEt): mp 162 to 164° C.; IR (CHCl$_3$) 2360, 1645 cm$^{-1}$; $^1$H-NMR (400 MHz, CDCl$_3$) δ 7.66 (2H, d, J=15.9 Hz), 6.98 (2H, d, J=15.9 Hz), 4.79 (2H, d, J=2.4 Hz), 3.92 (12H, s), 2.45 (2H, d, J=2.4 Hz); $^{13}$C-NMR (100 Hz, CDCl$_3$) δ 188.4, 153.8, 143.3, 137.8, 131.0, 125.0, 105.6, 79.0, 75.1, 60.0, 56.3; MS m/z 462 (M$^+$), 58 (100%); HRMR calcd for $C_{27}H_{26}O_7$ 462.1679, found: 462.1695. Anal. Calcd for $C_{27}H_{26}O_7$: C, 70.12; H, 5.67. Found: C, 70.07; H, 5.47.

(27) (1E,4E)-1-(4-methoxyphenyl)-5-(3,4,5-trimethoxyphenyl)penta-1,4-dien-3-one (GO-Y049)

Yellow oil: IR (CHCl$_3$) 1648 cm$^{-1}$; $^1$H-NMR (400 MHz, CDCl$_3$) δ 7.71 (1H, d, J=15.9 Hz), 7.63 (1H, d, J=15.9 Hz), 7.56 (2H, d, J=8.8 Hz), 6.98 (1H, d, J=15.9 Hz), 6.96 (1H, d, J=15.9 Hz), 6.93 (2H, d, J=8.8 Hz), 6.83 (2H, s), 3.91 (6H, s), 3.89 (3H, s), 3.83 (3H, s); $^{13}$C-NMR (100 Hz, CDCl$_3$) δ 188.5, 161.6, 153.4, 142.9, 142.8, 140.2, 130.3, 130.0, 127.4, 125.1, 123.0, 114.3, 105.5, 60.9, 56.1, 55.3; MS m/z 354 (M$^+$), 354 (100%); HRMR calcd for $C_{21}H_{22}O_5$ 354.1467, found: 354.1461.

(28) (1E,4E)-5-(3,4-dimethoxyphenyl)-1-(3-hydroxy-4-methoxyphenyl)penta-1,4-dien-3-one (GO-Y050)

Yellow amorphous: IR (CHCl$_3$) 3409, 1643 cm$^{-1}$; $^1$H-NMR (400 MHz, CDCl$_3$) δ 7.68 (1H, d, J=15.9 Hz), 7.66 (1H, d, J=15.7 Hz), 7.25 (1H, d, J=1.6 Hz), 7.20 (1H, d, J=8.2 Hz), 7.14 (1H, s), 7.11 (1H, d, J=8.5 Hz), 6.97 (1H, d, J=15.7

Hz), 6.92 (1H, d, J=15.9 Hz), 6.90 (1H, s), 6.89 (1H, d, J=8.0 Hz), 6.86 (1H, d, J=8.5 Hz), 5.78 (1H s), 3.94 (3H, s), 3.93 (3H, s), 3.93 (3H, s); $^{13}$C-NMR (100 Hz, CDCl$_3$) δ 188.7, 151.3, 149.2, 148.7, 145.9, 143.0, 142.8, 128.6, 127.9, 124.0, 123.6, 123.0, 122.5, 113.0, 111.1, 110.6, 109.9, 56.0, 56.0, 55.9; MS m/z 340 (M$^+$), 340 (100%); HRMR calcd for C$_{20}$H$_{20}$O$_5$ 340.1311 found: 340.1312.

(29) (1E,4E)-5-(3,4-dimethoxyphenyl)-1-(4-hydroxy-3-methoxyphenyl)penta-1,4-dien-3-one (GO-Y051)

Yellow amorphous: IR (CHCl$_3$) 3411, 1640 cm$^{-1}$; $^1$H-NMR (400 MHz, CDCl$_3$) δ 7.70 (1H, d, J=15.7 Hz), 7.66 (1H, d, J=15.7 Hz), 7.19 (1H, dd, J=8.2, 1.9 Hz), 7.17 (1H, dd, J=8.2, 1.9 Hz), 7.13 (1H, d, J=2.0 Hz), 7.12 (1H, d, J=1.9 Hz), 6.96 (1H, d, J=8.3 Hz), 6.95 (1H, d, J=15.9 Hz), 6.93 (1H, d, J=15.7 Hz), 6.89 (1H, d, J=8.5 Hz), 6.10 (1H s), 3.94 (3H, s), 3.94 (3H, s), 3.92 (3H, s); $^{13}$C-NMR (100 Hz, CDCl$_3$) δ 188.7, 151.3, 149.2, 148.2, 146.8, 143.2, 143.0, 127.8, 127.4, 123.6, 123.3, 123.3, 123.0, 114.9, 111.1, 110.0, 109.8, 55.9, 55.9; MS m/z 340 (M$^+$), 340 (100%); HRMR calcd for C$_{20}$H$_{20}$O$_5$ 340.1311, found: 340.1308.

(30) (1E,4E)-5-(3,4-dimethoxyphenyl)-1-[3-(1-ethoxyethoxy)-4-methoxyphenyl]penta-1,4-dien-3-one (GO-Y052)

Yellow oil: IR (CHCl$_3$) 1649 cm$^{-1}$; $^1$H-NMR (400 MHz, CDCl$_3$) δ 7.69 (1H, d, J=16.0 Hz), 7.67 (1H, d, J=15.9 Hz), 7.40 (1H, d, J=2.2 Hz), 7.28 (1H, dd, J=8.5 1.9 Hz), 7.20 (1H, dd, J=8.0 1.9 Hz), 7.15 (1H, d, J=1.9 Hz), 6.95 (2H, d, J=16.0 Hz), 6.91 (1H, d, J=8.2 Hz), 6.89 (1H, d, J=8.5 Hz), 5.42 (1H, q, J=5.3 Hz), 3.95 (3H, s), 3.93 (3H, s), 3.90 (3H, s), 4.0-3.9 (1H, m), 3.7-3.5 (1Hm), 1.55 (3H d, J=5.3 Hz), 1.24 (3H t, J=7.0 Hz); $^{13}$C-NMR (100 Hz, CDCl$_3$) δ 188.6, 153.0, 151.3, 149.2, 146.0, 143.0, 142.7, 127.9, 127.8, 124.4, 123.7, 123.6, 123.0, 128.3, 111.9, 111.1, 109.9, 101.1, 61.9, 55.9, 55.9, 55.9, 20.2, 15.1; MS m/z 412 (M$^+$), 340 (100%); HRMR calcd for C$_{24}$H$_{28}$O$_6$ 412.1886, found: 412.1877.

(31) (1E,4E)-5-(3,4-dimethoxyphenyl)-1-[4-(1-ethoxyethoxy)-3-methoxyphenyl]penta-1,4-dien-3-one (GO-Y053)

Yellow oil: IR (CHCl$_3$) 1646 cm$^{-1}$; $^1$H-NMR (400 MHz, CDCl$_3$) δ 7.69 (1H, d, J=15.7 Hz), 7.69 (1H, d, J=15.7 Hz), 7.21 (1H, d, J=8.3 Hz), 7.17 (1H, d, J=8.2 Hz), 7.15 (1H, d, J=1.7 Hz), 7.14 (1H, d, J=1.9 Hz), 7.12 (1H, d, J=8.2 Hz), 6.97 (1H, d, J=15.9 Hz), 6.96 (1H, d, J=15.9 Hz), 6.90 (1H, d, J=8.2 Hz), 5.45 (1H, q, J=5.3 Hz), 3.95 (3H, s), 3.94 (3H, s), 3.92 (3H, s), 3.95-3.80 (1H, m), 3.65-3.50 (1H m), 1.54 (3H d, J=5.1 Hz), 1.21 (3H t, J=7.0 Hz); $^{13}$C-NMR (100 Hz, CDCl$_3$) δ 188.5, 151.3, 150.1, 149.2, 148.2, 143.0, 142.7, 129.3, 127.7, 124.0, 123.5, 123.0, 122.3, 118.2, 111.0, 111.0, 109.9, 100.8, 61.8, 55.8, 55.8, 20.1, 15.0; MS m/z 340 (100%).

(32) (1E,4E)-1-(4-hydroxy-3-methoxyphenyl)-5-(3-methoxy-4-methoxymethoxyphenyl)penta-1,4-dien-3-one (GO-Y055)

Yellow amorphous solid; IR (CHCl$_3$): 3390, 1644 cm$^{-1}$; $^1$H-NMR (400 MHz, CDCl$_3$) δ=7.20-7.11 (5H, m), 6.98-6.92 (3H, m), 5.94 (1H, s), 5.28 (2H, s), 3.96 (3H, s), 3.94 (3H, s), 3.53 (3H, s); $^{13}$C-NMR (100 Hz, CDCl$_3$) δ=188.7, 149.9, 148.2, 146.8, 143.3, 142.8, 141.5, 129.3, 127.5, 124.2, 123.4, 123.3, 122.5, 115.9, 114.9, 110.8, 109.8, 95.2, 56.4, 56.0, 56.0; MS m/z 370 (M$^+$); HRMS Calcd C$_{21}$H$_{22}$O$_6$: 370.1416, Found: 370.1402.

(33) (1E,4E)-1-(3-hydroxy-4-methoxyphenyl)-5-(3-methoxy-4-methoxymethoxyphenyl)penta-1,4-dien-3-one (GO-Y056)

Yellow amorphous solid; IR (CHCl$_3$): 3583, 1644 cm$^{-1}$; $^1$H-NMR (400 MHz, CDCl$_3$) δ=7.67 (1H, d, J=15.9 Hz), 7.65 (1H, d, J=16.7 Hz), 7.25 (1H, d, J=2.2 Hz), 7.17-7.10 (4H, m), 6.99-6.86 (3H, m), 5.68 (1H, s), 5.28 (2H, s), 3.94 (6H, s), 3.53 (3H, s); $^{13}$C-NMR (100 Hz, CDCl$_3$) δ=188.7, 170.1, 148.8, 146.0, 142.9, 142.8, 124.6, 123.6, 122.6, 122.5, 116.0, 113.0, 110.8, 110.6, 95.3, 56.4, 56.0, 55.9; MS m/z 370 (M$^+$); HRMS Calcd C$_{21}$H$_{22}$O$_6$: 370.1416, Found: 370.1418.

(34) (1E,4E)-1-[3-(1-ethoxyethoxy)-4-methoxyphenyl]-5-(3-methoxy-4-methoxymethoxyphenyl)penta-1,4-dien-3-one (GO-Y057)

Yellow oil; IR (CHCl$_3$): 1646 cm$^{-1}$; $^1$H-NMR (400 MHz, CDCl$_3$) δ=7.68 (1H, d, J=15.9 Hz), 7.67 (1H, d, J=16.0 Hz), 7.40 (1H, d, J=2.1 Hz), 7.27 (1H, dd, J=8.7, 1.9 Hz), 7.18-7.16 (3H, m), 6.96 (1H, d, J=15.7 Hz), 6.94 (1H, d, J=15.5 Hz), 6.91 (1H, d, J=8.2 Hz), 5.42 (1H, dd, J=9.6, 5.4 Hz), 5.28 (2H, s), 3.95 (3H, s), 3.90 (3H, s), 3.87 (1H, m), 3.61 (1H, m), 3.59 (3H, s), 2.54 (3H, d, J=5.7 Hz), 1.22 (1H, t, J=7.0 Hz); $^{13}$C-NMR (100 Hz, CDCl$_3$) δ=188.6, 153.0, 149.9, 148.7, 146.1, 142.9, 142.8, 129.3, 127.9, 124.5, 124.3, 123.6, 122.6, 118.4, 115.9, 111.9, 110.7, 101.1, 95.2, 62.0, 56.3, 56.0, 55.9; MS m/z 442 (M$^+$); HRMS Calcd C$_{25}$H$_{30}$O$_7$: 442.1992, Found: 442.2001.

(35) (1E,4E)-1-[4-(1-ethoxyethoxy)-3-methoxyphenyl]-5-(3-methoxy-4-methoxymethoxyphenyl)penta-1,4-dien-3-one (GO-Y058)

Yellow oil; IR (CHCl$_3$): 1648 cm$^{-1}$; $^1$H-NMR (400 MHz, CDCl$_3$) δ=7.69 (2H, d, J=15.9 Hz) 7.21 (2H, dd, J=8.2, 1.7 Hz), 7.15 (2H, d, J=1.69 Hz), 6.96 (2H, d, J=15.9 Hz), 6.90 (2H, d, J=8.2 Hz), 3.95 (6H, s), 3.93 (6H, s); $^{13}$C-NMR (100 Hz, CDCl$_3$) δ=188.0, 175.0, 148.6, 142.4, 135.0, 127.3, 123.1, 122.5, 110.7, 109.5, 72.8, 55.8, 55.7; MS m/z 397 ([M-C$_2$H$_5$O]$^+$).

(36) (1E,4E)-1-(3,5-dimethoxy-4-prop-2-ynyloxyphenyl)-5-(3,4,5-trimethoxyphenyl)penta-1,4-dien-3-one (GO-Y060)

Yellow needles (AcOEt), mp=118 to 120° C.; IR (CHCl$_3$): 3258, 1649 cm$^{-1}$; $^1$H-NMR (400 MHz, CDCl$_3$) δ=7.66 (2H, d, J=15.1 Hz), 6.98 (1H, d, J=15.6 Hz), 6.97 (1H, d, J=15.1 Hz), 6.85 (4H, s), 6.78 (2H, d, J=2.4 Hz), 3.92 (12H, s), 3.90 (3H, s), 2.45 (1H, t, J=2.4 Hz); $^{13}$C-NMR (100 Hz, CDCl$_3$) δ=188.4, 153.8, 153.5, 143.4, 143.2, 131.0, 130.2, 125.0, 124.8, 105.7, 105.6, 79.1, 75.1, 61.0, 60.0, 56.3, 56.2; MS m/z 438 (M$^+$); HRMS Calcd. C$_{25}$H$_{26}$O$_7$: 438.1679, Found: 438.1670.

(37) (1E,4E)-1-(3,5-bis-methoxymethoxyphenyl)-5-(3,5-dimethoxy-4-prop-2-ynyloxyphenyl)penta-1,4-dien-3-one (GO-Y062)

Yellow amorphous; IR (CHCl$_3$): 3283, 1650 cm$^{-1}$; $^1$H-NMR (400 MHz, CDCl$_3$) δ7 =7.66 (1H, d, J=15.9 Hz), 7.65 (1H, d, J=16.0 Hz), 7.04 (1H, d, J=16.0 Hz), 6.98 (1H, d, J=16.0 Hz), 6.97 (2H, d, J=2.2 Hz), 6.86 (2H, s), 6.79 (1H, t, J=2.3 Hz), 5.20 (4H, s), 4.79 (2H, d, J=2.4 Hz), 3.93 (6H, s), 3.50 (6H, s), 2.46 (1H, t, J=2.4 Hz); $^{13}$C-NMR (100 Hz, CDCl$_3$) δ=188.6, 158.6, 153.8, 143.4, 142.9, 137.8, 136.9, 130.9, 126.0, 109.5, 107.1, 105.5, 94.5, 77.2, 75.1, 60.0, 56.3, 56.1; MS m/z 468 (M$^+$); HRMS Calcd C$_{26}$H$_{28}$O$_8$: 468.1784, Found: 468.1798.

(38) (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063)

Yellow amorphous; IR (CHCl$_3$): 3268, 1649 cm$^{-1}$; $^1$H-NMR (400 MHz, CDCl$_3$) 67 =7.66 (2H, d, J=15.9 Hz), 6.98 (2H, dd, J=15.8, 5.2 Hz), 6.85 (4H, s), 5.18 (2H, s), 4.78 (2H, d, J=2.4 Hz), 3.91 (6H, s), 3.91 (6H, s), 3.61 (3H, s), 2.46 (1H, t, J=2.4 Hz); $^{13}$C-NMR (100 Hz, CDCl$_3$) δ=188.4, 153.8, 153.6, 143.4, 143.2, 131.0, 130.7, 125.0, 124.8, 105.6, 98.2, 79.0, 75.1, 60.0, 57.2, 56.3, 56.1; MS m/z 468 (M$^+$); HRMR Calcd C$_{26}$H$_{28}$O$_8$: 468.1784, Found: 468.1786.

(39) (1E,4E)-1,5-bis-[4-(2-azidoethoxy)-3,5-dimethoxyphenyl]penta-1,4-dien-3-one (GO-Y065)

Yellow columns (CHCl$_3$/Hexane), mp=107 to 109° C.; IR (CHCl$_3$): 2105, 1649 cm$^{-1}$; $^1$H-NMR (400 MHz, CDCl$_3$) δ=7.66 (2H, d, J=15.7 Hz), 6.98 (2H, d, J=16.0 Hz), 6.85 (4H, s), 4.20 (4H, t, J=5.1 Hz), 3.92 (12H, s), 3.56 (2H, t, J=5.1 Hz); $^{13}$C-NMR (100 Hz, CDCl$_3$) δ=188.4, 153.5, 143.3, 138.8, 130.7, 124.9, 105.5, 71.7, 56.2, 51.1; MS m/z 525 ([M+H]$^+$); FIRMS Calcd C$_{25}$H$_{29}$N$_6$O$_7$: 525.2098, Found: 525.2106; Anal. Calcd. C$_{25}$H$_{28}$N$_6$O$_7$: C, 57.25; H, 5.38; N, 16.02, Found: C, 57.02; H, 5.68; N, 16.03.

(40) (1E,4E)-1,5-bis-(3,5-dimethoxymethoxyphenyl)penta-1,4-dien-3-one (GO-Y067)

Yellow columns (AcOEt/Hexane), mp=130 to 132° C.; IR (CHCl$_3$): 1653 cm$^{-1}$; $^1$H-NMR (400 MHz, CDCl$_3$) δ=7.61 (2H, d, J=15.9 Hz), 7.00 (2H, d, J=15.8 Hz), 6.85 (4H, d, J=2.2 Hz), 6.49 (2H, t, J=2.2 Hz), 3.81 (12H, s); $^{13}$C-NMR (100 Hz, CDCl$_3$) δ=188.6, 160.9, 143.2, 136.5, 125.7, 106.2, 102.7, 55.4; MS m/z 354 (M$^+$); FIRMS Calcd C$_{21}$H$_{22}$O$_5$: 354.1467, Found: 354.1474; Anal. Calcd.: C$_{21}$H$_{22}$O$_5$: C, 71.17; H, 6.26, Found: C, 70.87; H, 6.24.

EXAMPLE 4

Cell Growth Inhibitory Activity

The inhibitory efficacy of bis(arylmethylidene)-acetones on the development and growth of malignant tumor cells was examined. Curcumin and bis(arylmethylidene)-acetone compounds were dissolved in DMSO to obtain 50 mM compound solutions for storage. Sixteen human cancer cell lines (HCT116, DLD-1, SW620. LK87, PC3, MCF7, PK9, HuCCT-1, SH10TC, GCIY, G361, 8505c, HepG2, A431, ACHN, OVK18) were obtained from the Medical Cellular Resources Center of the Institute of Development, Aging, and Cancer at Tohoku University, Japan. These cells were cultured at 37° C. under 5% CO$_2$ conditions using as a culture medium RPMI1640 (Sigma Aldrich) supplemented with 10% fetal bovine serum and kanamycin (Wako Pure Chemical Industries: final concentration, 60 pg/mL).

Three human colon-cancer cell lines (DLD-1, HCT116, SW620) were used in screening for cell growth inhibitory efficacy. The test compounds (bis(arylmethylidene)-acetones) were added to the culture media at the target concentrations, and exposure to the compounds was then continued for 96 hours in order to investigate not only acute cell damages but also effects on the cells, involving intracellular metabolic responses and others. The cell growth inhibitory efficacy was then evaluated with Cell Counting Kit 8 (Wst-8 Test, Dojindo Laboratories, Japan). In this analysis method, tetrazolium salt Wst-8 is degraded by reduced form nicotinamide adenine dinucleotide (nicotinamide adenine dinucleotide H; NADH). The activity of NADH is maintained only inside viable cells, and Wst-8 becomes colored upon degradation. The optical absorbance at 450 nm is measured, whereby the number of viable cells can be indirectly estimated.

Each cell line was placed on a 96-well microtiter plate at a cell density of 2500 to 5000 cells/100 μL/well in accordance with the growth rate of the cell line. After cell cultivation for 24 hours, 100 of medium containing each compound was added. The final concentration of each test compound is 0, 0.1, 0.25, 0.5, 1, 2.5, 5, 10, 25, 50, and 100 μM (11 levels). The maximum final concentration of DMSO used as a solvent was 1%. After culturing for 96 hours, the medium was aspirated away, followed by washing with PBS. Next, 100 μL of a medium containing a solution of Cell Counting Kit 8 at 1/10 (v/v) was added. Culturing was then continued for one hour. Thereafter, each optical absorbance at 450 nm (620 nm background) was measured with an MPR-A4i microplate reader (Tosoh, Japan). A curve of the inhibition of cell growth was constructed using the measured optical absorbances. The IC$_{50}$ concentration at which the number of viable cells is 50% of the number of cells non-treated with test compounds (controls) was calculated from the curve.

Curcumin and those compounds that exerted a strong inhibitory efficacy on the growth of cells in comparison to curcumin were then used to analyze similarly the cell growth inhibitory effect on the remaining 13 cell lines. Stored solutions of three anti-cancer agents: 5-FU, CDDP, and CPT11, prepared beforehand (1 mM), were suitably diluted prior to use, and also added to culture media.

Test compounds were examined for the cell growth inhibitory activity on colon-cancer cell line HCT116. The concentrations at which cell growth is limited to 50% relative to controls (1050 values) are shown in FIGS. 1, 3, and 4. The majority of the newly synthesized bis(arylmethylidene)-acetones had lower IC50 concentrations than that of curcumin (IC50: 8.0 μM). In other words, these compounds have stronger activity in inhibiting the growth of malignant tumor cells. Among these compounds, 1,5-bis(3,4,5-trimethoxyphenyl)-1,4-pentadien-3-one (BTMP, GO-Y016) wherein a methoxy group is added to each 5-carbon atom on the 1- and 5-benzene rings, 1,5-bis(3,5-dimethoxy-4-methoxymethoxyphenyl)-1,4-pentadien-3-one (BDMMMPP, GO-Y031) wherein each 4-methoxy group on the benzene rings of BTMP is replaced with a methoxymethoxy group, and 1,5-bis[3,5-bis(methoxymethoxy)phenyl]-1,4-pentadien-3-one (BBMMPP, GO-Y030) wherein each 4-methoxy group on the 1- and 5-benzene rings at both ends of BDMMMPP is replaced with hydrogen and 3- and 5-methoxy groups thereon are replaced with methoxymethoxy groups exert strong inhibitory activity in the growth of tumor cells (FIG. 1).

Figure 5A:
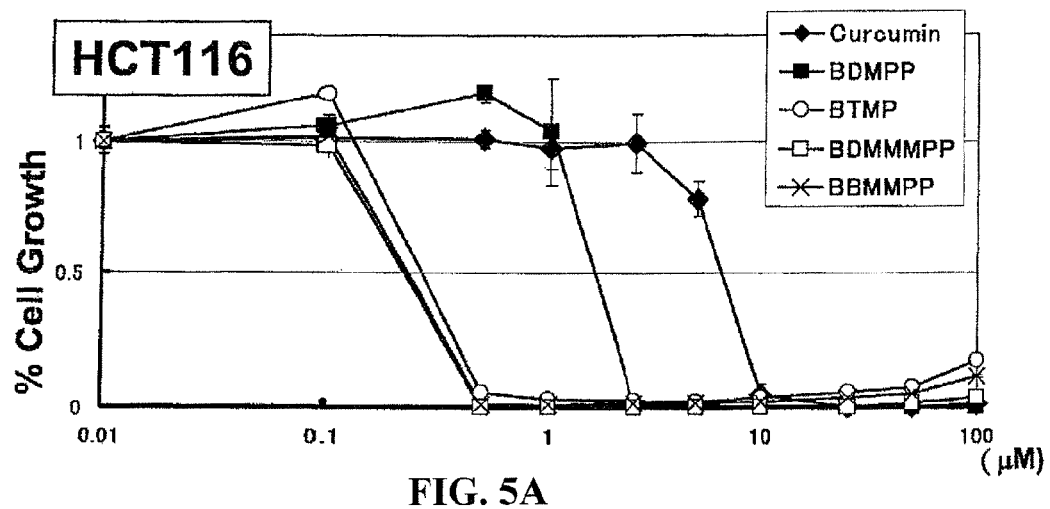
FIGS. 5A-5C show the effects of inhibiting growth (IC50) of HCT116, SW620, and DLD-1 colon cancer cells for curcumin, BDMPP (GO-035), BTMP (GO-Y016), BDMMMPP (GO-Y031), and BBMMPP (GO-Y030)
Figure 5B:
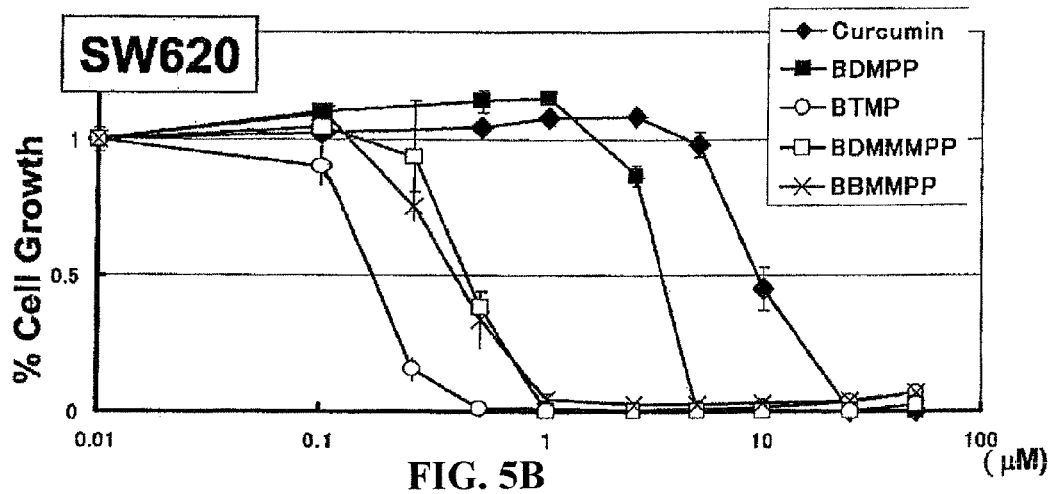
Figure 5C:
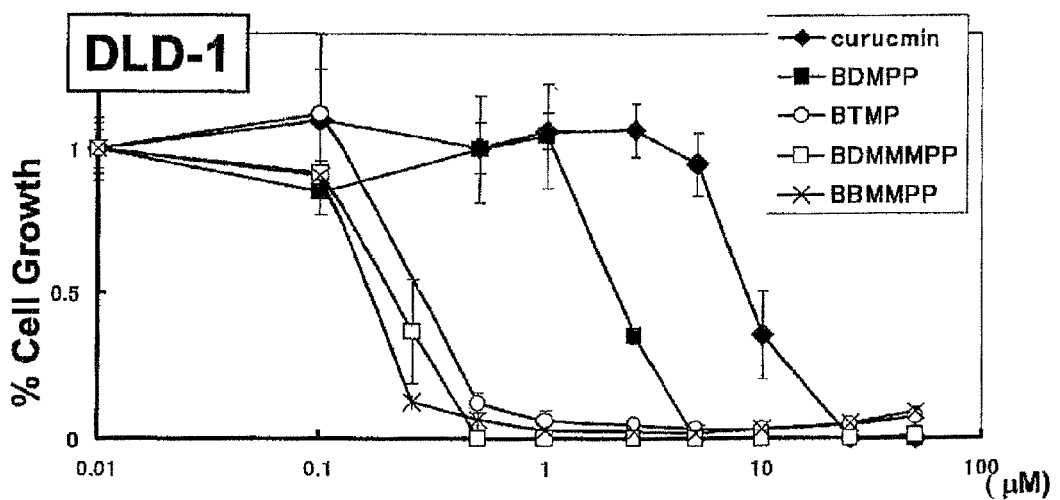

FIG. 5 shows the results of investigations on the IC50s for BTMP, BDMMMPP, and BBMMPP against SW620 and DLD-1 cells, which are other cell lines derived from colon cancer.

BTMP, BDMMMPP, and BBMMPP all had 1050, 0.25 μM against HCT116 cells. These cell growth inhibitory effects exceed curcumin IC50 8.0-μM and BDMPP IC50 2.5-μM against HCT116 cells by factors of approximately 10 to 40.

The 1050 for BTMP, BDMMPP, and BBMMPP against SW620 cells was 0.20, 0.50, and 0.55 µM, respectively. These values exceed curcumin IC50 10.0-µM and BDMPP IC50 3.5-µM against SW620 cells. The IC50 for BTMP, BDMMPP, and BBMMPP against DLD-1 cells were 0.25, 0.25, and 0.30 µM, respectively. These values exceed curcumin IC50 8.0-µM and BDMPP IC50 2.0-µM against DLD-1 cells by factors of approximately 8 to 32.

Figure 6:
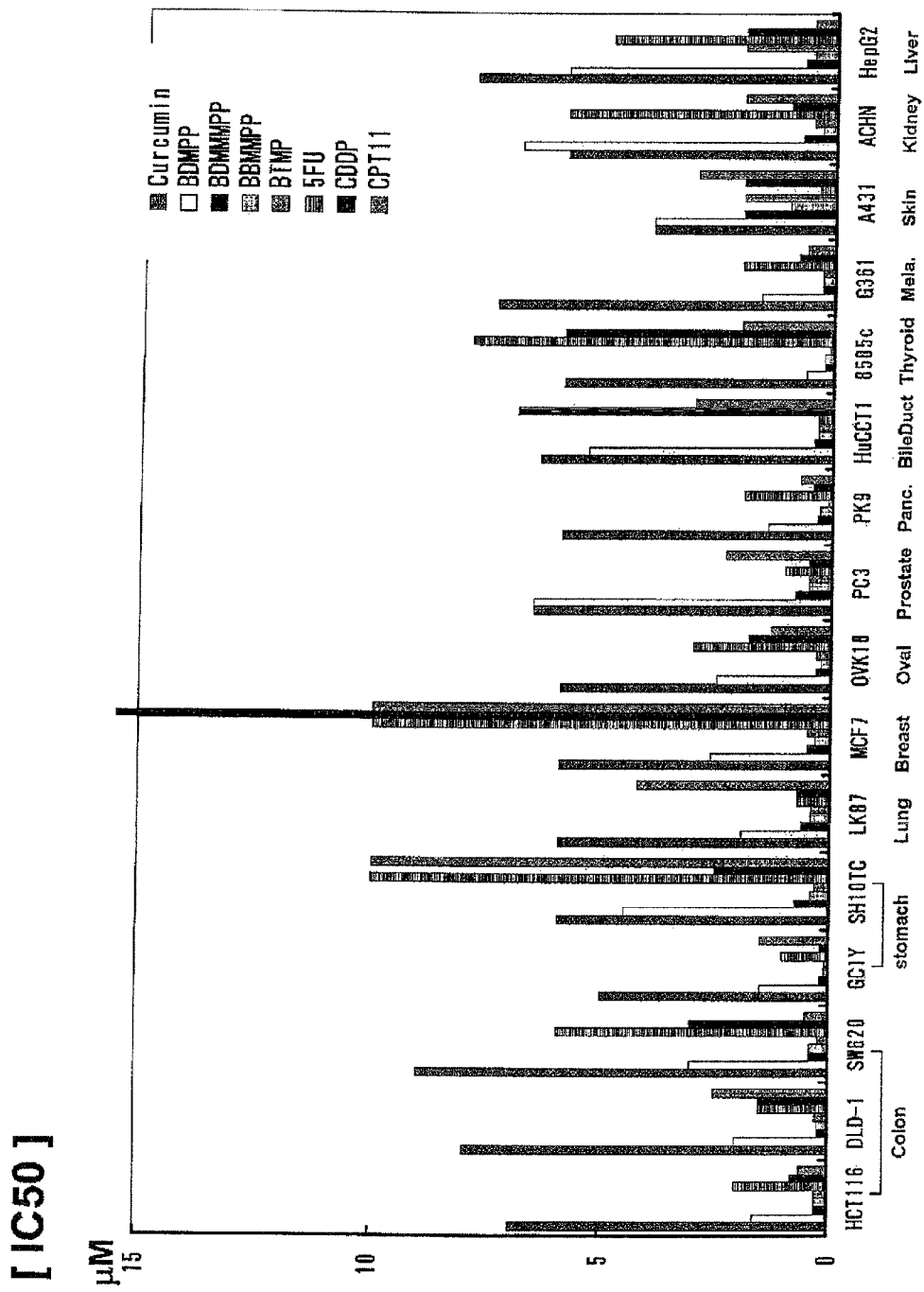
FIG. 6 shows a comparison of the effects of inhibiting growth (IC50) of cancer cells for curcumin, BDMPP (GO-035), BTMP (GO-Y016), BDMMMPP (GO-Y031), and BBMMPP (GO-Y030) versus those of various anti-cancer agents (5FU, CDDP, CPT11)

The inhibitory activities of GO-035 (BDMPP), GO-Y016 (BTMP), GO-Y031 (BDMMPP), and GO-Y030 (BBMMPP) in the growth of colon-cancer cells was shown to be much stronger than those of 5-FU, irinotecan hydrochloride (CPT11), and cisplatin (CDDP), which are widely clinically applicable anti-cancer agents (FIG. 6). The inventive compounds, GO-Y016 (BTMP), GO-Y031 (BDMMPP), and GO-Y030 (BBMMPP), also exert strong anti-cancer activity relative to 5-FU, CPT11, and CDDP against cell lines derived not only from colon cancer but from a variety of other cancers, such as stomach cancer, lung cancer, breast cancer, ovarian cancer, prostate cancer, pancreatic cancer, bile duct cancer, thyroid cancer, and melanoma (FIG. 6).

In FIG. 6, HCT116, DLD1, and SW620 cell lines are derived from colon cancer, GCIY and SH10TC cells derived from stomach cancer, LK87 cells derived from lung cancer, MCF7 cells derived from breast cancer, OVK18 cells derived from ovarian cancer, PC3 cells derived from prostate cancer, PK9 cells derived from pancreatic cancer, HuCCT1 cells derived from bile duct cancer, 8505c cells derived from thyroid cancer, G361 cells derived from melanoma, A431 cells derived from skin cancer, ACHN cells derived from kidney cancer, and HepG2 cells derived from liver cancer, respectively. The inventive compounds, BTMP, BDMMPP, and BBMMPP, do not exert biological effects surpassing conventional anti-cancer agents against A431, ACHN, and HepG2 cells, but it is demonstrated that these compounds can serve as therapeutic drugs for colon cancer and many other cancers.

EXAMPLE 5

Apoptosis-Inducing Activity

The activity of test compounds in cell cycle (apoptosis-inducing activity) was analyzed with a flow cytometer (FAC-Scan). Curcumin (20 µM) and the bis(arylmethylidene)-acetone compounds, GO-035 (5 µM), GO-Y016 (1 µM), GO-Y030 (2 µM), and GO-Y031 (2 µM), were added to HCT-116 cells ($5\times10^5$ cells/well) media, and the cells were cultured on 6-well cell-culture plates. The cells attached to the plates are then harvested together with the cells suspended in the medium, centrifuged, and pelleted, followed by removal of supernatants. The collected cells were washed twice with PBS, then fixed with 70% ethanol for 30 minutes or more at 4° C., then washed with PBS once more, suspended in PBS supplemented with RNaseA (final concentration: 50 µg/mL; Qiagen), and incubated for 20 minutes at 37° C. Centrifugation was performed, and the supernatant was removed, after which the nuclei were stained using a solution of propidium iodide (50 µL/mL). Filtration was then performed using a nylon mesh having a pore size of 50 µm, and a DNA histogram was analyzed with a FACScan flow cytometer (Beckman Coulter). The cellular fractions of $subG_1$ phase, $G_0/G_1$ phase, S phase, and $G_2/M$ phase were determined by calculation using macCycle (Phoenix Flow Systems).

When the effect on the cell cycle of DLD-1 cells was analyzed using flow cytometry, GO-035 (BDMPP) was found to arrest the cell cycle at the G2/M phase at 5 µM, and GO-Y016 (BTMP), GO-Y031 (BDMMPP), and GO-Y030 (BBMMPP) were found to do so at low concentrations of 1 to 2 µM (FIG. 7), respectively. In particular, 2-µM BDMMPP and BBMMPP increased the sub-G1 fraction corresponding to apoptosis-induced cell death 20 to 26%, which is strong apoptosis-inducing activity in comparison to curcumin, for which a sub-G1 fraction was not substantially observed (FIG. 7).

EXAMPLE 6

Analysis of Effects on Expression of Oncogene Products

Western-blot analysis was used to investigate effects on the expression of oncogene products, ErbB2, c-Myc, and Cyclin D1, whose activity is enhanced in a variety of cancer cells, and to investigate the activity of degrading β-catenin, which plays an important role in the initial stages of carcinogenesis to the formation and development of tumors.

Western-blot analysis was performed in the following manner:

After HCT116 cells were treated with each test compound, plate-adhered cells were recovered along with cells suspended in supernatants, centrifuged, and pelleted. The cells were then lysed with a lysis solution (40 mM Tris-HCl, 1% Triton X-100, 2 mM $MgCl_2$) supplemented with 200-µM phenylmethanesulfonyl fluoride (PMSF), 500-µM benzamidine, and 1-µg/mL leupeptin. After the mixture was allowed to stand on ice for 30 minutes, it was centrifuged for 10 minutes at 4° C. and 10000×g, and supernatants were recovered. To the resultant supernatant was added equimolarly 2× sample buffer (0.1 M Tris-HCl (pH 6.8), 4% SDS, 20% glycerol, and 12% β-mercaptoethanol), and the mixture was shaken for 3 minutes at 4° C., then heated to 95° C. for 4 minutes, and then stored at −20° C. until use. The cell lysates were phoresed on 8% SDS-PAGE, transferred to a Hybond-P membrane (Amersham Biosciences), and made to react with various monoclonal antibodies described below.

Monoclonal antibodies: anti-actin antibody (A2066, Sigma Aldrich), anti-β-catenin antibody (6101 53, BD-transduction Laboratories), anti-p53 antibody (FL393: sc-6243HRP), anti-cyclin D1 antibody (M-20: sc-718), anti-c-Myc antibody (9E10: sc-40), anti-k-Ras-2B antibody (C-19: sc-521), and anti-c-ErbB2 antibody (A0485, DAKO Cytomation).

Figure 8:
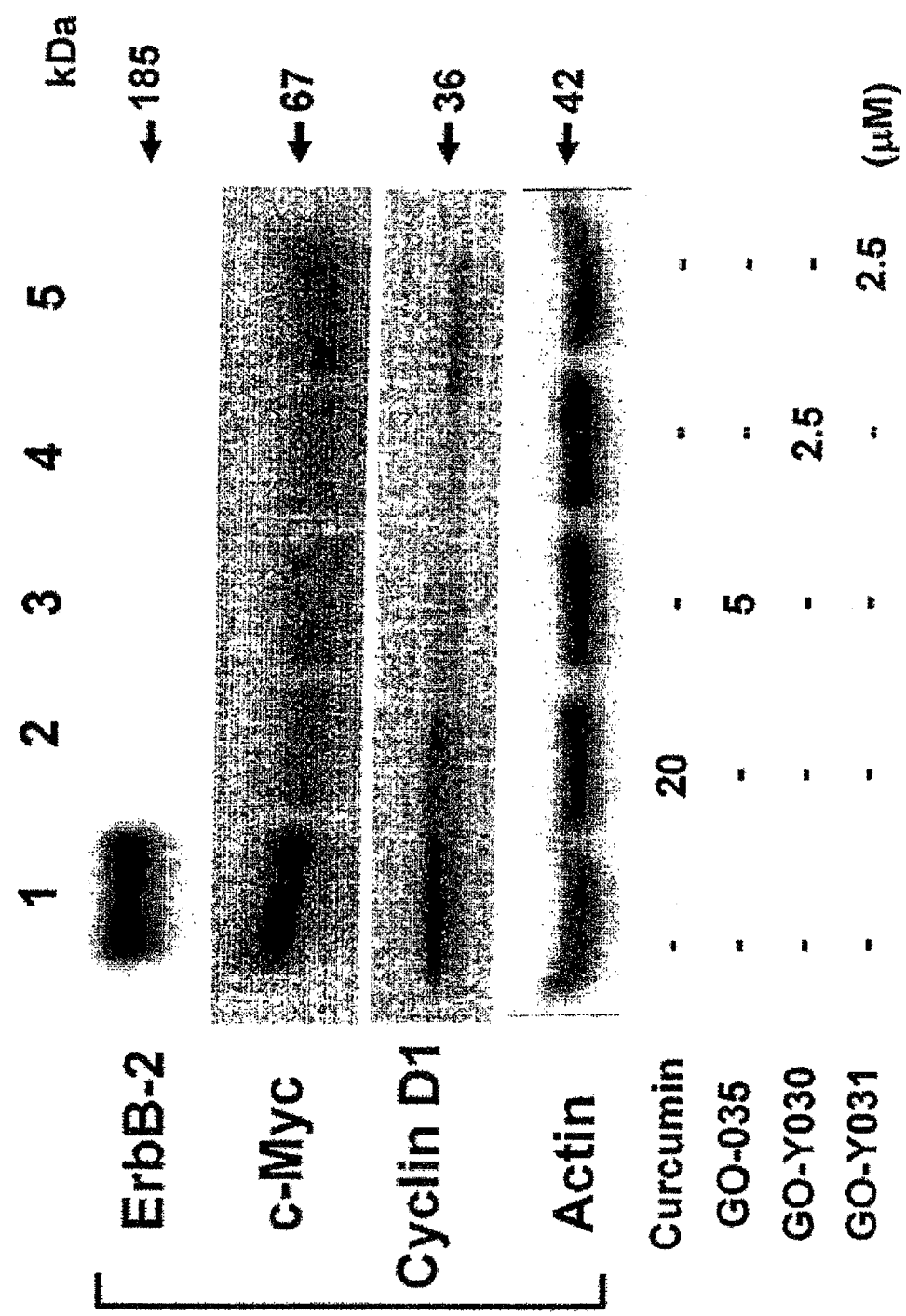
FIG. 8 is a Western blot analysis of the effects of curcumin, BDMPP (GO-035), BBMMPP (GO-Y030), and BDMMMPP (GO-Y031) on the expression of ErbB2, c-Myc, and Cyclin D1, which are oncogene products.

Curcumin is well-known to reduce the expression levels of oncogene products, ErbB2, c-Myc, and Cyclin D1, whose activity is enhanced in a variety of cancer cells. This effect is thought to be one of the mechanisms by which curcumin inhibits cancer-cell growth. The newly synthesized compounds, GO-Y030 (BBMMPP) and GO-Y031 (BDMMPP), exerted an effect equal to or greater than curcumin at concentrations that were lower than that of curcumin by a factor of 8 or more when the efficacy of GO-Y030 (BBMMPP) and GO-Y031 (BDMMPP) on the expression level of these oncogene products was analyzed (FIG. 8).

Figure 9:
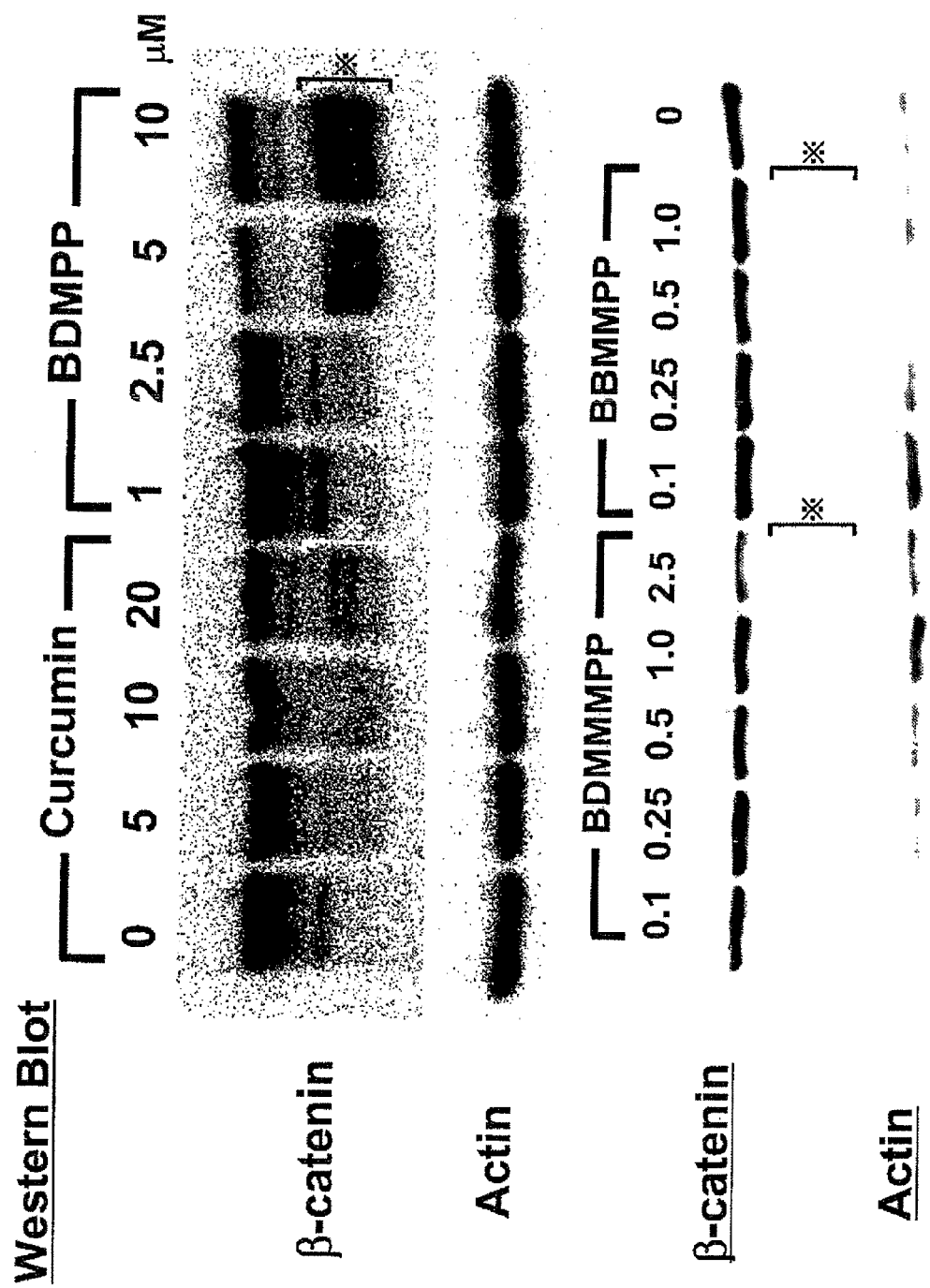
FIG. 9 is a Western-blot analysis of the $\beta$-catenin degrading activity of curcumin, BDMPP (GO-035), BDMMMPP (GO-Y031), and BBMMPP (GO-Y030), wherein $\beta$-catenin degrading activity is displayed at low concentrations of 5 $\mu$M BDMPP (GO-035) and 1 $\mu$M BDMMMPP (GO-Y031) and BBMMPP (GO-Y030), and the "*" designates degraded $\beta$-catenin.

Curcumin is also well-known to exert the effect of degrading β-catenin, which plays an important role in the initial carcinogenic stages to tumor formation for colon cancer (Non-Patent Document 1). In human familial adenomatous polyposis, hundreds or thousands of adenomas grow in the colon, and colon cancer readily develops from among these adenomas. A 40% inhibition of the formation of tumors has been verified when curcumin was orally administered to mouse models of human familial adenomatous polyposis (Non-Patent Document 3). It is thought that this activity of curcumin could be applied as a chemical anti-carcinogenic agent. The bis(aryl-methylidene)-acetones of the present invention are closely-related derivatives of curcumin and can be expected to have β-catenin-degrading activity and concomitant effects of preventing carcinogenesis that are equal to or greater than curcumin. The β-catenin-degrading activity of GO-035 (BDMPP), which has the basic skeleton of a bis (arylmethylidene)-acetone, was investigated first. Curcumin begins to exert β-catenin-degrading activity at 20.0 μM, but the analysis showed that intracellular β-catenin is already degraded at a low concentration of 5.0-μM GO-035 (BDMPP) (FIG. 9).

The strong β-catenin-degrading activity of GO-035 (BDMPP) was newly discovered in the present work. The chemopreventive activity of BDMPP exceeds that of curcumin, indicating that BDMPP could be used as a strong chemopreventive agent. The β-catenin-degrading activities of GO-Y016 (BTMP), GO-Y031 (BDMMMPP), and GO-Y030 (BBMMPP) were also investigated. The results revealed that BDMMMPP and BBMMPP (but not BTMP) have β-catenin-degrading activity that is equal to or greater than that of BDMPP (FIG. 9). The new discovery of the β-catenin-degrading activity and other properties of BDMPP and the other newly synthesized bis(arylmethylidene)-acetones in this work indicates that these compounds could be used as chemical agents for preventing the genesis of colon cancer. The effects of the bis(arylmethylidene)-acetones of the present invention as chemo-preventive agents are not particularly limited to colon cancer but are thought to be widely applicable to preventing the genesis of any cancer in which excessive expression of β-catenin is linked to carcinogenesis.

Figure 10:
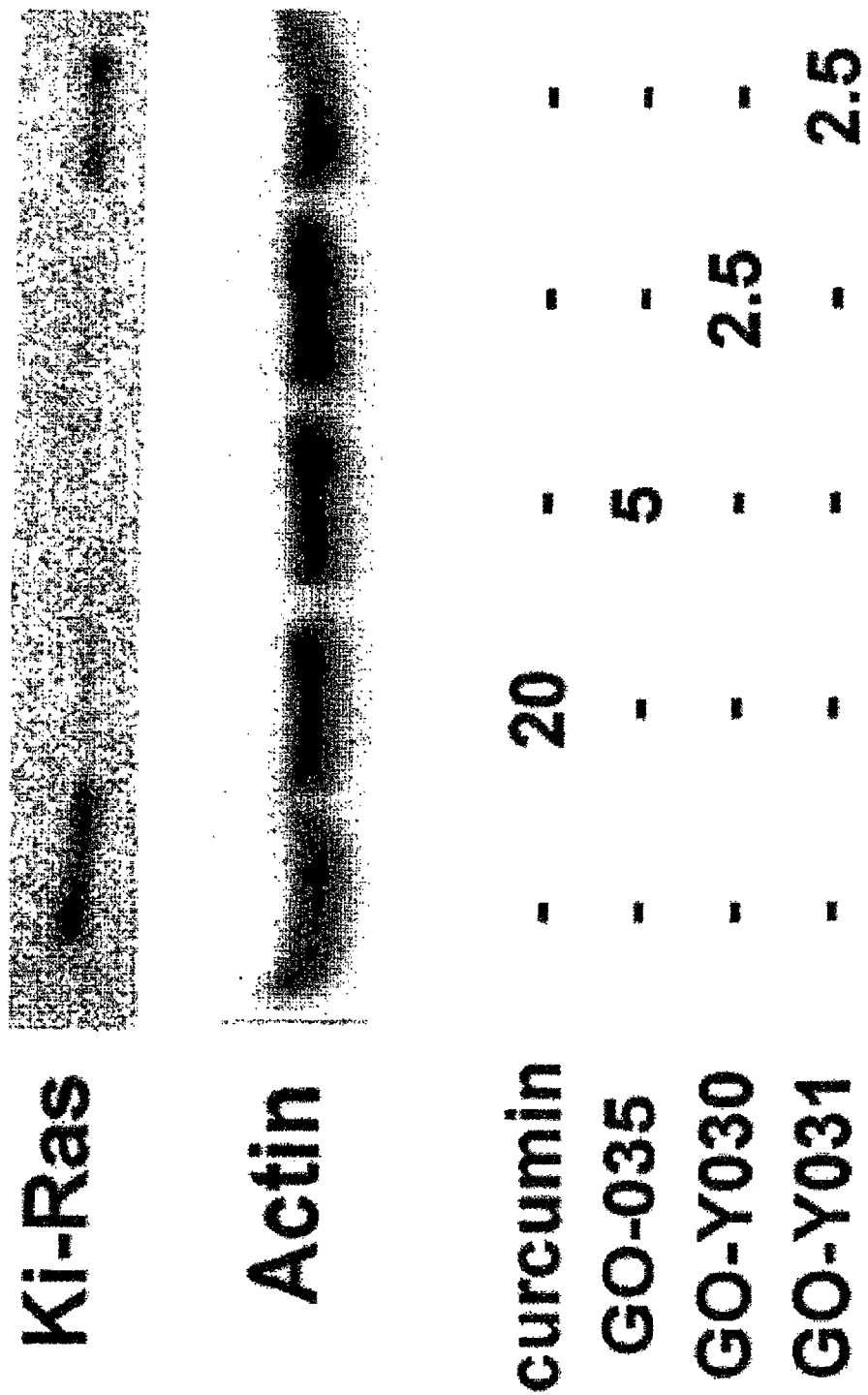
FIG. 10 shows the results of a Western blot analysis of the inhibition of expression of the Ki-Ras oncogene product by curcumin, GO-035 (BDMPP), GO-Y030 (BBMMPP), and GO-Y031 (BDMMMPP)

The Ki-Ras oncogene causes activating mutations in numerous cancer cells. The activating mutations of the Ki-Ras oncogene are closely linked to the transition to cancer. The Ki-Ras oncogene is a gene mutation found when the initial adenomas transition to adenomas of intermediate malignancy in the carcinogenic process of the colon. It was shown that GO-035 (BDMPP) as well as newly synthesized GO-Y030 (BBMMPP) and GO-Y031 (BDMMMPP), also including curcumin, had activity in reducing the expression of Ki-Ras oncogene products in the present work. These results indicate that these novel compounds function in inhibiting the processes of carcinogenesis in the colon both in degrading β-catenin and in reducing the expression of the Ki-Ras oncogene product. GO-Y030 (BBMMPP) in particular exerted an efficacy equal to or greater than that of curcumin at concentrations that were less than curcumin by a factor of 8 or more (FIG. 10).

Figure 11:
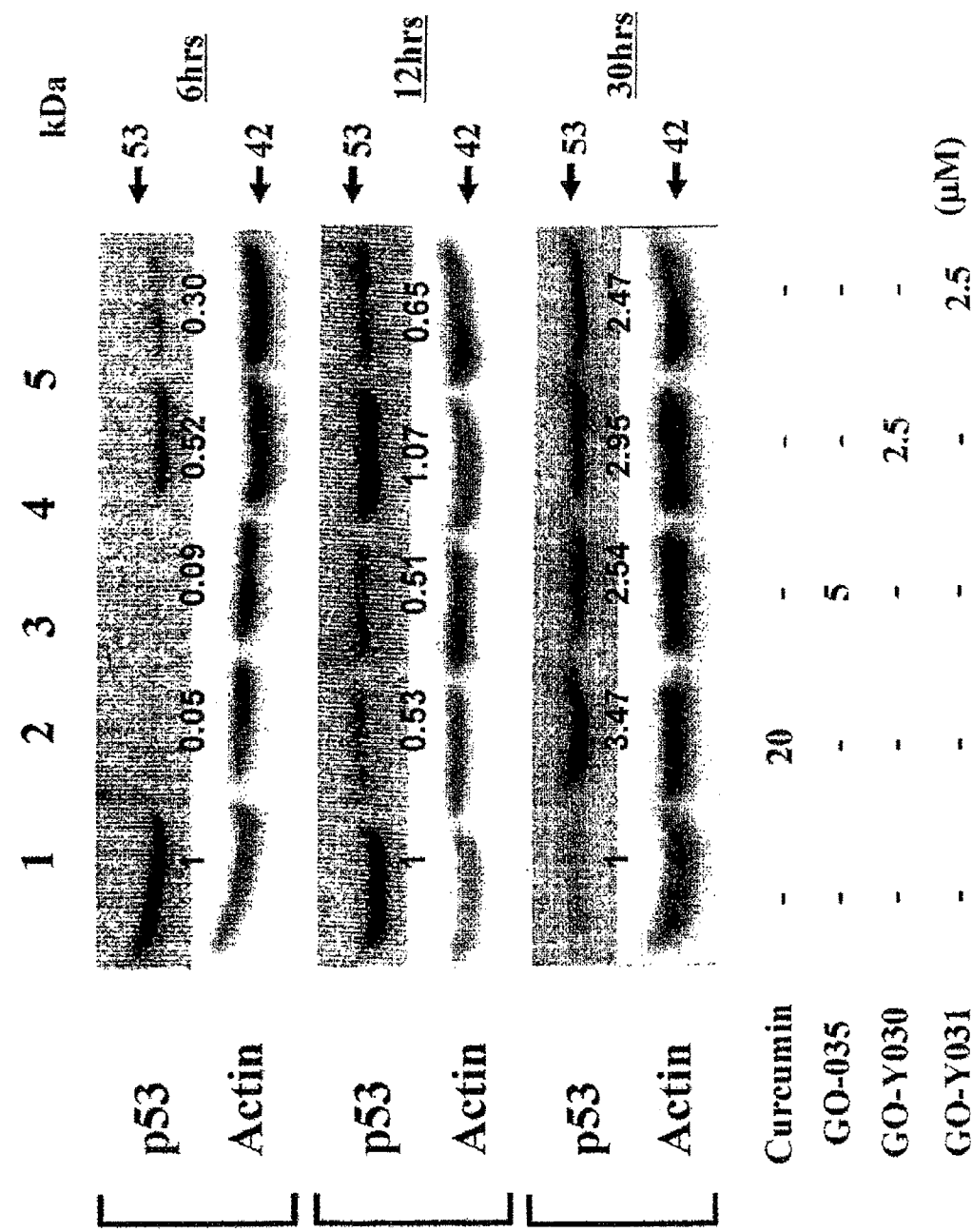
FIG. 11 shows the results of a Western blot analysis of the stabilization and over expression of the p53 gene product by curcumin, GO-035 (BDMPP), GO-Y030 (BBMMPP), and GO-Y031 (BDMMMPP), wherein the numbers are the amount of expression under various conditions relative to a value of 1 for a p53 control, the transient drop in expression of p53 6 to 12 hours after administration of curcumin was not seen for GO-Y030 (BBMMPP) and GO-Y031 (BDMMMPP), and enhanced expression of p53 was induced after 30 hours.

Curcumin is known to have activity in degrading p53 gene products. Degradation, genetic expression reduction, instability, or other deficiencies of the tumor suppressor gene p53 gene products, result in disadvantageous conditions as concerns cell malignancy and tendency to become cancerous. The newly synthesized BBMMPP (GO-Y030) and BDMMMPP (GO-Y031) have less effects on transient gene expression decrease and instability of p53 relative to curcumin and BDMPP (GO-035), and after 30 hours induce enhanced expression of p53 (FIG. 11).

EXAMPLE 7

Analysis of Caspase-3 Induction

A caspase-3/8 inhibitor (N-CBZ-Asp-Glu-Val-Asp-Fluoromethyl ketone, Z-DEVD-fmk, Sigma Aldrich) was added to media (final concentration, 20 μM) and allowed to stand in an incubator for 1 hour. Each test compound was then added, followed by cultivation. Cells were recovered in the same fashion as above, and Western blot and FACScan analyses were performed.

The activity of caspase-3 was evaluated as follows:

The induction of caspase-3 activity due to curcumin and bis(arylmethylidene)-acetone compounds was measured with a caspase-3 cellular activity assay kit (EMD Biosciences). The method used will be briefly explained. After HCT116 cells ($5 \times 10^5$ cells/well per 6-well plate) were cultured for 24 hours, the compound was added, followed by cultivation for another 24 hours. Supernatant and adherent cells were then recovered and centrifuged. The supernatants were completely removed, and the cells suspended in 50 μL of RPMI1640 culture media, transferred to 96-well microtiter plates, allowed to stand at −80° C. for 30 minutes or more, and then thawed on ice for 30 minutes. To the frozen-thawed samples was added 100 μL of analysis buffer (0.1 M HEPES, pH 7.5, 10% sucrose, 5 mM DTT, $10^{-6}$% NP40, 0.1% CHAPS) and the cells were lysed by pipetting. To the cell lysate was added 2.5 mM acetyl-Asp-Glu-Val-Asp-7-amino-4-methylcoumarin (Ac-D E V D-AMC), which is a substrate for caspase-3, at 1 μL, and the degradation products resulting from cleavage reactions due to caspase-3 were examined over the course of time (every minute) for 30 minutes with a Fluoroskan (Thermo Labsystems, 355-nm excitation, 460-nm emission). Calibration was conducted using 1 μM and 2 μM AMC.

Figure 12:
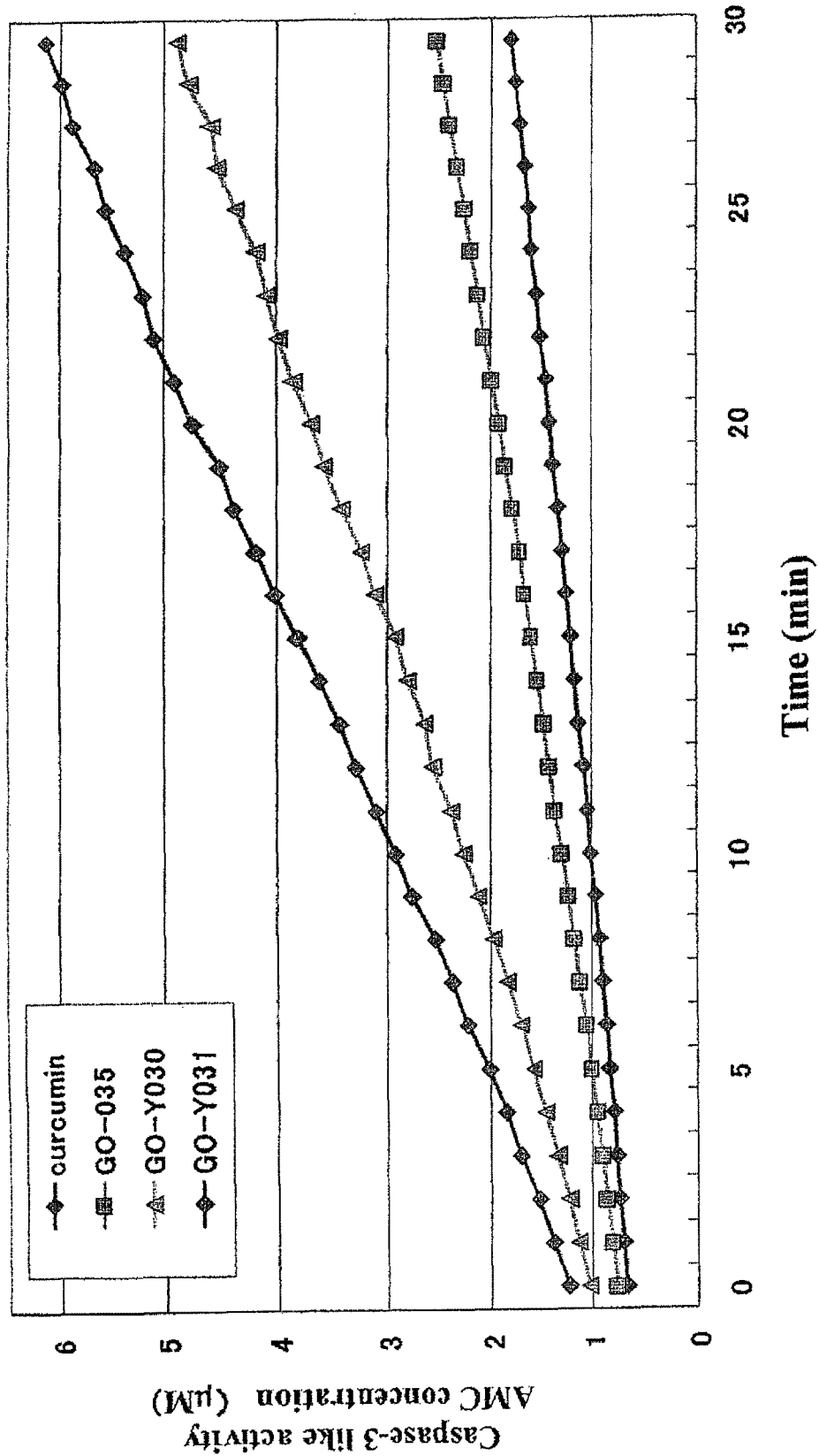
FIG. 12 is an analysis of the ability of 10-$\mu$M curcumin, 5-$\mu$M GO-035 (BDMPP), and 2.5-$\mu$M GO-Y030 (BBMMPP) and GO-Y031 (BDMMMPP) to induce caspase-3 after treating colon cancer cells with these compounds for 24 hours.
Figure 13A:
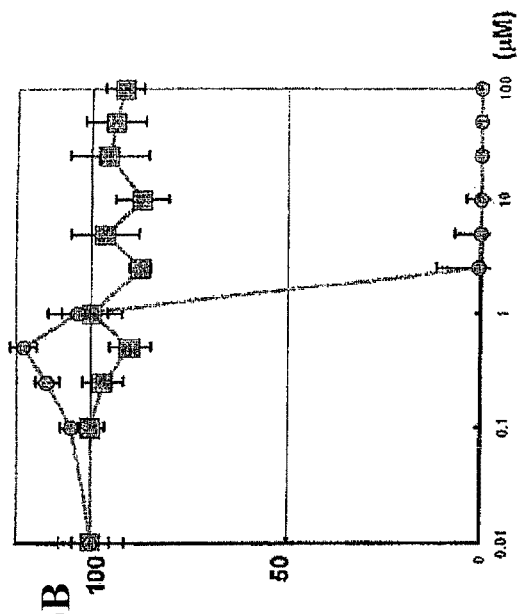
FIGS. 13A-13D show experiments on limitation of growth of and instigation of damage to normal cells by (A) curcumin, (B) GO-035 (BDMPP), (C) GO-Y030 (BBMMPP), and (D) GO-Y031 (BDMMMPP)
Figure 13B:
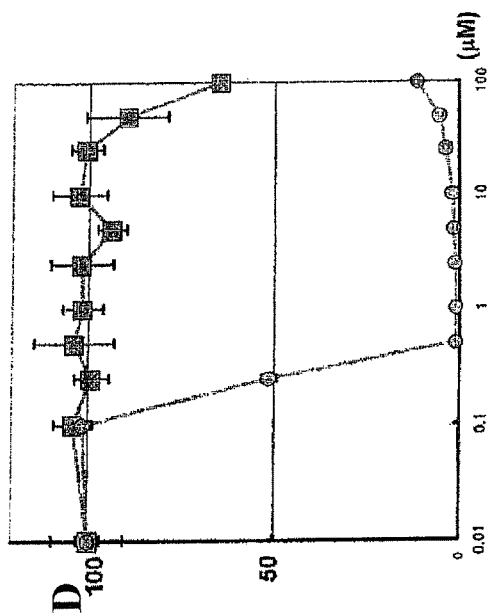
Figure 13C:
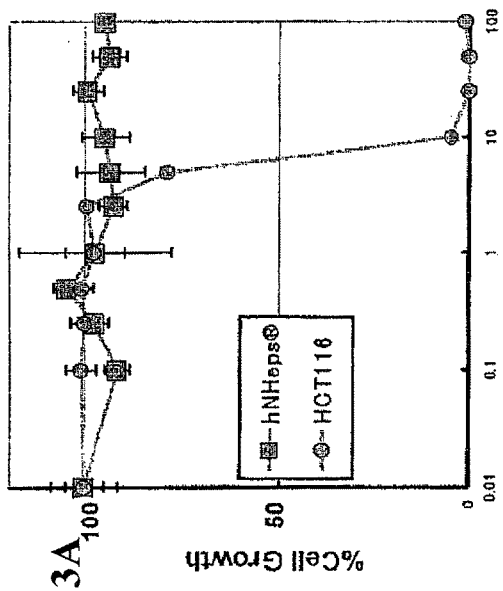
Figure 13D:
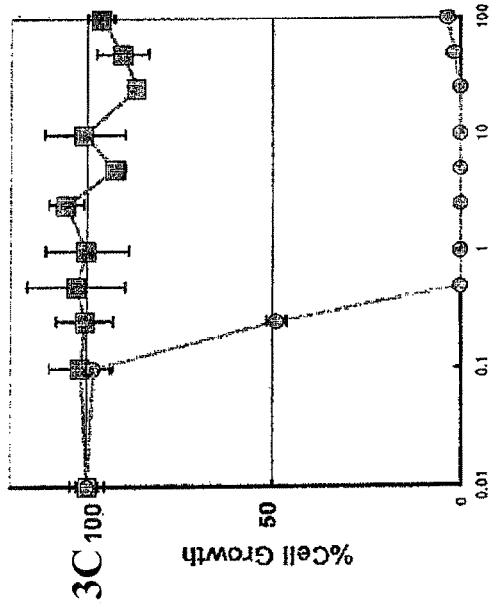

Colon cancer cells were treated for 24 hours with 10 μM curcumin, 5 BDMPP, and 2.5 μM BDMMMPP and BBMMPP, respectively, and the induction of caspase-3 by these compounds was analyzed. The cells were lysed in a cell lysis solution. To the solution was added Ac-DEVD-aminomethylcoumarin, which is a substrate for caspase-3, and the generation of cleaved products was measured continuously using a Fluoroskan. The results are shown in FIG. 12. The slopes in the graphs correspond to the induced activity of caspase-3.

EXAMPLE 8

Test for Evaluating Toxicity

Figures 14A, 14B:
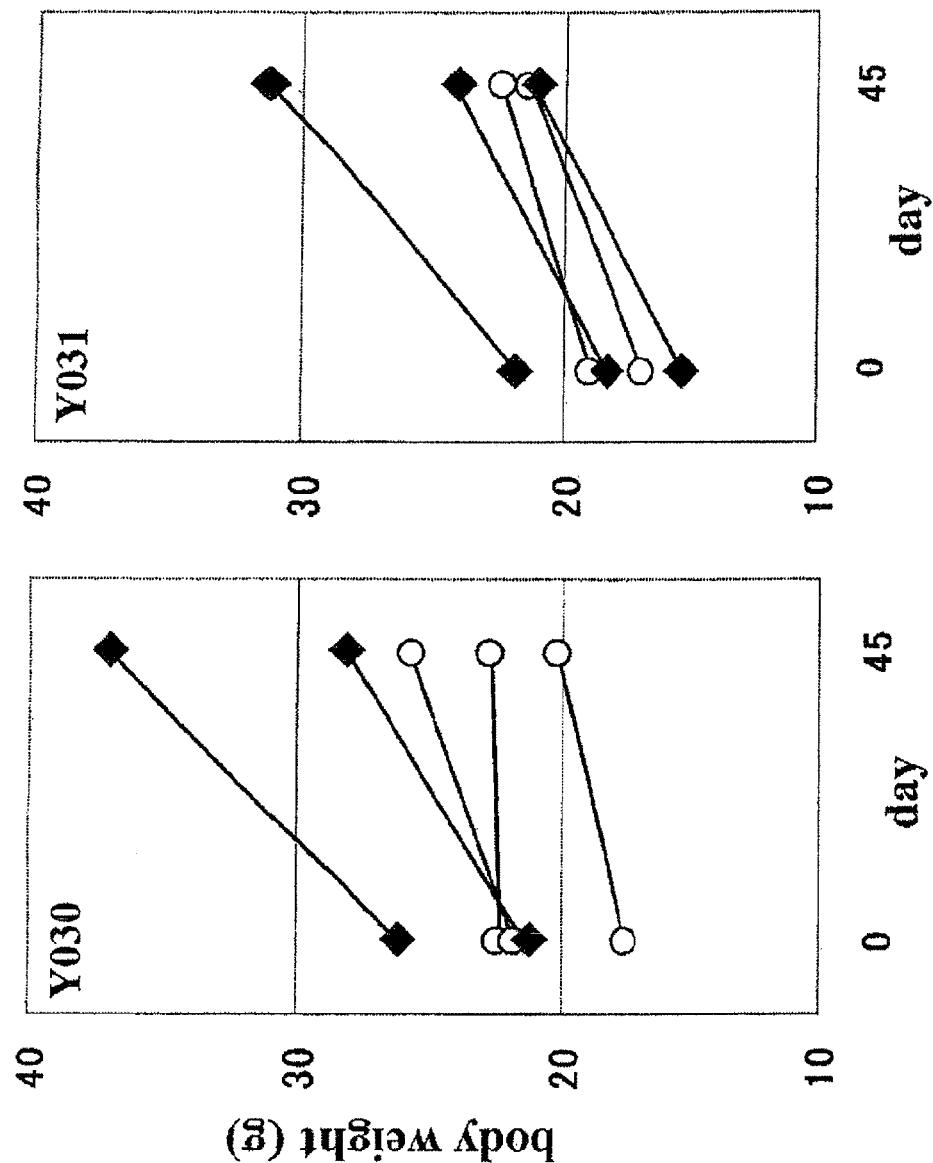
FIGS. 14A and 14B show the results of experiments in which GO-Y030 (BBMMPP) and GO-Y031 (BDMMMPP) were administered to mice, and changes in individuals' body weight were evaluated.

The synthetic compounds of the present invention are derived from curcumin, which is originally a food item. These compounds can be expected to maintain the low toxic property that is characteristic of curcumin. When BBMMPP (GO-Y030) and BDMMMPP (GO-Y031) were tested using primary cultured hepatic cells (hNHeps™ (Cambrex)), no growth inhibition was observed on normal cells in which no activation of cancer-related genes was seen. It was also observed that these compounds were non-cytotoxic (FIG. 13). As a further test for in vivo toxicity, inbred C57BL/6J mice received daily an oral intake of 5 g of mixed feed (test compound dose: 5 mg/day) wherein each test compound was admixed at 0.1% (weight/weight) with a high-fat diet (HFD35, CLEA Japan). No bodily abnormalities, including weight loss, were observed, as shown in FIG. 14. Administration is continuing for at least more than 120 days, but no particular abnormalities have been seen.

EXAMPLE 9

Activity in Models of Familial Adenomatous Polyposis

As aforementioned, BBMMPP (GO-Y030) and BDMMMPP (GO-Y031) are expected to be active as chemopreventive agents against colon cancers due to reducing or extinguishing the expression of both β-catenin gene products and Ki-Ras oncogene products. β-catenin gene products are involved in the initiation of carcinogenesis in the colon, and Ki-Ras oncogene products are seen to be abnormally activated when the initial adenomas are converted into adenomas of intermediate malignancy. Familial adenomatous polyposis (FAP) is the most appropriate model for considering the multistage process of carcinogenesis in colon cancer. The APC gene is a causative gene in this illness. This gene is a tumor suppressor gene and is linked to the degradation of the β-catenin gene product. The FAP mouse model Aoc580D (Apc580D/+mice, wherein a mutation was introduced into the mouse Apc gene by homologous genetic recombination) is heterozygous for a genetic mutation in which codon 580 of the APC gene is a stop codon (i.e., the Apc gene product is truncated at codon 580). These mice present hundreds of polyps in the gastrointestinal tract in the same manner as human FAP. Polyps can be seen starting at ages of 4 to 5 weeks, and these mice die from blood loss or intestinal obstruction due to the adenomas at an average age of 18.3 weeks (128 days) when fed a normal diet. Reference: Shibata H. et al., Science, 278, pp. 120-123 "Rapid colorectal adenoma formation initiated by conditional targeting of the Apc gene," 1997.

These FAP model Apc580D mice were given daily an oral intake of high-fat diet HFD35 admixed with 0.1% (w/w) BBMMPP (GO-Y030) or BDMMMPP (GO-Y031) at a dose of 5 g (test compound dose: 5 mg/day). Analysis was performed on therapeutic models (in which administration was initiated around the age of 8 weeks, when polyposis had already been observed) and prophylactic models (in which administration was initiated around the age of 4 weeks, when polyposis had not been observed) of carcinogenesis in the colon. Apc580D mice (2 animals) given daily an oral intake of HFD35 alone at a dose of 5 g were used as a control.

Figure 15:
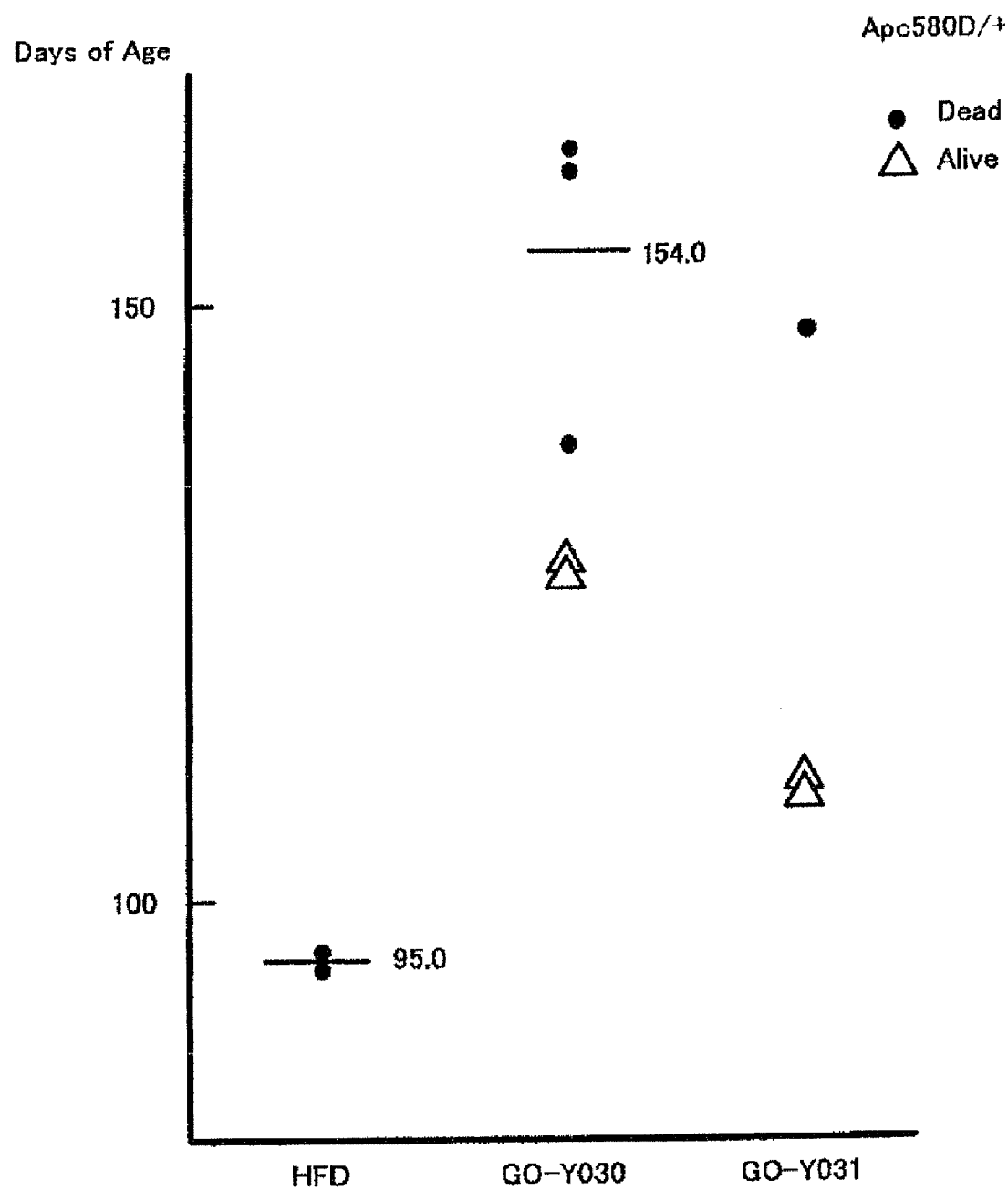
FIG. 15 shows the results of experiments in which GO-Y030 (BBMMPP) and GO-Y031 (BDMMMPP) were administered to familial adenomatous polyposis mouse model Apc580D, wherein the survival time when only high-fat diet HFD32 was administered to Apc580D mice is shown by black circles on the left, the survival time when BBMMPP (GO-Y030) was administered to treatment models (black circles) and anti-carcinogenic models (white triangles; still surviving) is shown in the center, and the survival time when BDMMMPP (GO-Y031) was administered to treatment models (black circles) and anti-carcinogenic models (white triangles; still surviving) is shown on the right.

A high-fat diet is a risk factor for carcinogenesis in the colon, and Apc580D mice fed only HFD35 died due to tumors at the age of 95 days, which is earlier than when the mice were fed on a normal diet. When BBMMPP (GO-Y030) was administered, however, the average survival time of the three therapeutic model mice was 154.0 days. The two anti-carcinogenically prophylactic model mice continued to survive for an average of 128.0 days or more and are currently still alive. In the case of BDMMMPP (GO-Y031), the single therapeutic model survived to 148.0 days. The two anti-carcinogenically prophylactic model mice continued to survive for an average of 110.0 days or more and are currently still alive (FIG. 15).

Both the therapeutic models and the prophylactic models survived longer when received BBMMPP (GO-Y030) and BDMMMPP (GO-Y031) in admixture with high-fat diet HFD35 than when fed on HFD35 alone. It is thought that these newly synthesized compounds are active in treating and preventing carcinogenesis in the colon.

INDUSTRIAL APPLICABILITY

According to the present invention, synthetic bis(arylmethylidene)acetone compounds have chemo-preventive activity and anti-tumor activity for inhibiting the growth of various cancers at low concentrations are provided. Bis(arylmethylidene)acetone derivatives which have the basic skeleton of anti-tumor and anti-carcinogenic curcumin, can be synthesized. The compounds thus produced can be widely used as anti-neoplastic agents and chemo-preventive agents.

While the present invention has been described specifically in detail with reference to certain embodiments and examples thereof, it would be apparent that it is possible to practice it in other forms. In light of the aforedescribed teachings, it will be understood that various modifications and variations are within the spirit and scope of the appended claims.

The invention claimed is:
1. An inhibitor of Ki-Ras, ErbB2, c-Myc, or Cyclin D1 expression; a β-catenin-degrading agent; a p53 expression enhancer; an anti-cancer agent; or a carcinogenesis chemo-preventive agent, which comprises an effective amount of a bis(arylmethylidene)-acetone compound having the Formula:

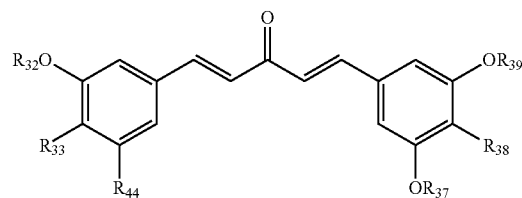

(wherein $R_{44}$ is a hydrogen atom or $OR_{34}$,
$R_{33}$ and $R_{38}$, which may be identical or different, are independently a member selected from the group consisting of a hydrogen atom, a halogen atom, a hydroxyl group, a nitro group, an alkoxy group, a hydroxy-alkoxy group, an alkoxyalkoxy group, an alkoxyalkoxyalkoxy group, an alkynyloxy group, and an azido-alkoxy group, or $R_{33}$ may be taken together with the adjacent substituent $OR_{32}$ or $OR_{34}$ to form an alkylene-dioxy bridge, and/or $R_{38}$ may be taken together with the adjacent substituent $OR_{37}$ or $OR_{39}$ to form an alkylene-dioxy bridge, and
$R_{32}$, $R_{34}$, $R_{37}$ or $R_{39}$, which may be identical or different, are independently a member selected from the group consisting of a hydrogen atom, an alkyl group, an alkynyl group, an alkoxyalkyl group, an alkoxyalkoxyalkyl group and an azido-alkyl group, or may be taken together with the adjacent substituent $R_{33}$ or $R_{38}$ to form the aforementioned bridge, provided that
(1) when $R_{44}$ is a hydrogen atom, $R_{32}=R_{39}=$an alkyl group, and $R_{33}=R_{38}=$an hydroxyl atom or an alkoxy group, and
(2) a compound wherein: (a) $R_{44}$ is $OR_{34}$, $R_{32}=R_{39}=$an alkyl group, and $R_{33}=R_{38}=$a member selected from a hydrogen atom and an alkoxy group, and (b) $R_{44}$ is $OCH_3$, $R_{32}=R_{37}=R_{39}=CH_3$, and $R_{33}=R_{38}=OH$ is excluded.
2. The inhibitor according to claim 1, wherein the bis (arylmethylidene)-acetone compound is selected from the group consisting of
(1E,4E)-1,5-bis-[3,5-bis(methoxymethoxy)phenyl]penta-1,4-dien-3-one (GO-Y030, BBMMPP),
(1E,4E)-1,5-bis-(3,5-dimethoxy-4-methoxymethoxyphenyl)penta-1,4-dien-3-one (GO-Y031, BDMMMPP),
(1E,4E)-1,5-bis-(3,5-dimethoxy-4-methoxy-ethoxymethoxy-phenyl)penta-1,4-dien-3-one (GO-Y039),
(1E,4E)-1,5-bis-[4-(2-hydroxyethoxy)-3,5-dimethoxy-phenyl]penta-1,4-dien-3-one (GO-Y044),
(1E,4E)-1-(3,4-dimethoxyphenyl)-5-(3,4,5-trimethoxy-phenyl)penta-1,4-dien-3-one (GO-Y046),
(1E,4E)-1,5-bis-(3,5-dimethoxy-4-prop-2-ynyloxy-phenyl)pentadien-3-one (GO-Y048),
(1E,4E)-1-(3,5-dimethoxy-4-prop-2-ynyloxyphenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxyphenyl)penta-1,4-dien-3-one (GO-Y062), (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063), (1E,4E)-1,5-bis-[4-(2-azidoethoxy)-3,5-dimethoxyphenyl]-penta-1,4-dien-3-one (GO-Y065), or a salt thereof.

3. A bis(arylmethylidene) acetone compound having the Formula:

[Chemical Structure 2]

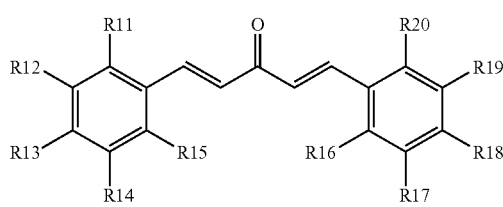

(2)

(wherein $R_{44}$ is hydrogen or $OR_{34}$, $R_{33}$ and $R_{38}$, which may be identical or different, are independently a member selected from the group consisting of a hydrogen atom, a halogen atom, an hydroxyl group, a nitro group, an alkoxy group, a hydroxy-alkoxy group, an alkoxyalkoxy group, an alkoxyalkoxyalkoxy group, an alkynyloxy group, and an azido-alkoxy group, or $R_{33}$ may be taken together with the adjacent substituent $OR_{32}$ or $OR_{34}$ to form an alkylene-dioxy bridge, and/or $R_{38}$ may be taken together with the adjacent substituent $OR_{37}$ or $OR_{39}$ to form an alkylene-dioxy bridge, and $R_{32}$, $R_{34}$, $R_{37}$ or $R_{39}$, which may be identical or different, are independently a member selected from the group consisting of a hydrogen atom, an alkyl group, an alkynyl group, an alkoxyalkyl group, an alkoxyalkoxyalkyl group and an azido-alkyl group, or may be taken together with the adjacent substituent $R_{33}$ or $R_{38}$ to form the aforementioned bridge, provided that (1) when $R_{44}$ is a hydrogen atom, $R_{32}=R_{39}=$an alkyl group, and $R_{33}=R_{38}=$a hydroxyl group or an alkoxy group, and (2) a compound wherein: (a) $R_{44}$ is $OR_{34}$, $R_{32}=R_{39}=$an alkyl group, and $R_{33}=R_{38}=$a member selected from a hydrogen group and an alkoxy group, and (b) $R_{44}$ is $OCH_3$, $R_{32}=R_{37}=R_{39}=CH_3$, and $R_{33}=R_{38}==OH$ is excluded.

4. The bis(arylmethylidene)-acetone compound according to claim 3 selected from the group consisting of (1E,4E)-1,5-bis-[3,5-bis(methoxymethoxy)phenyl]penta-1,4-dien-3-one (GO-Y030, BBMMPP), (1E,4E)-1,5-bis-(3,5-dimethoxy-4-methoxymethoxyphenyl)penta-1,4-dien-3-one (GO-Y031, BDMMMPP), (1E,4E)-1,5-bis-(3,5-dimethoxy-4-methoxyethoxymethoxy-phenyl)penta-1,4-dien-3-one (GO-Y039), (1E,4E)-1,5-bis-[4-(2-hydroxyethoxy)-3,5-dimethoxyphenyl]penta-1,4-dien-3-one (GO-Y044), (1E,4E)-1-(3,4-dimethoxyphenyl)-5-(3,4,5-trimethoxyphenyl)penta-1,4-dien-3-one (GO-Y046), (1E,4E)-1,5-bis-(3,5-dimethoxy-4-prop-2-ynyloxy-phenyl)pentadien-3-one (GO-Y048), (1E,4E)-1-(3,5-dimethoxy-4-prop-2-ynyloxyphenyl)-5-(3,4,5-trimethoxyphenyl)penta-1,4-dien-3-one (GO-Y060), (1E,4E)-1-(3,5-bis-methoxymethoxyphenyl)-5-(3,5-dimethoxy-4-prop-2-ynyloxyphenyl)penta-1,4-dien-3-one (GO-Y062), (1E,4E)-1-(3,5-dimethoxy-4-methoxymethoxyphenyl)-5-(3,5-dimethoxy-4-prop-2-ynyloxyphenyl)penta-1,4-dien-3-one (GO-Y063), (1E,4E)-1,5-bis-[4-(2-azidoethoxy)-3,5-dimethoxyphenyl]-penta-1,4-dien-3-one (GO-Y065), or a salt thereof.

* * * * *

UNITED STATES PATENT AND TRADEMARK OFFICE
CERTIFICATE OF CORRECTION

PATENT NO.        : 8,178,727 B2
APPLICATION NO.   : 11/993840
DATED             : May 15, 2012
INVENTOR(S)       : Shibata et al.

It is certified that error appears in the above-identified patent and that said Letters Patent is hereby corrected as shown below:

In Drawings, Figure 4, Compound GO-Y063, Column R4 "H" should be -- –OCH$_3$--

IN THE CLAIMS:

At Column 37, Lines 15-23, Claim 3:

The chemical structure in claim 3 should be as follows:

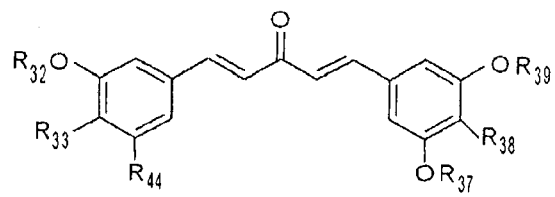

-- --

Signed and Sealed this
Nineteenth Day of March, 2013

Teresa Stanek Rea
*Acting Director of the United States Patent and Trademark Office*